(12) United States Patent
Scheib et al.

(10) Patent No.: US 11,058,508 B2
(45) Date of Patent: Jul. 13, 2021

(54) STERILE ADAPTER FOR A LINEARLY-ACTUATING INSTRUMENT DRIVER

(71) Applicant: VERB SURGICAL INC., Mountain View, CA (US)

(72) Inventors: Charles J. Scheib, Loveland, OH (US); Andrea Bajo, Palo Alto, CA (US); Kent M. Anderson, Mountain View, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 393 days.

(21) Appl. No.: 16/020,547

(22) Filed: Jun. 27, 2018

(65) Prior Publication Data
US 2019/0000580 A1 Jan. 3, 2019

Related U.S. Application Data

(60) Provisional application No. 62/526,871, filed on Jun. 29, 2017.

(51) Int. Cl.
*A61B 34/30* (2016.01)
*A61B 46/10* (2016.01)
*A61B 17/00* (2006.01)

(52) U.S. Cl.
CPC ............ *A61B 46/10* (2016.02); *A61B 17/00* (2013.01); *A61B 34/30* (2016.02);
(Continued)

(58) Field of Classification Search
CPC ......... A61B 46/10; A61B 34/30; A61B 17/00; A61B 2034/305; A61B 2017/00477; A61B 2017/00862
(Continued)

(56) References Cited

U.S. PATENT DOCUMENTS

| 6,132,368 A | 10/2000 | Cooper |
| 6,345,072 B1 | 2/2002 | Liu et al. |

(Continued)

FOREIGN PATENT DOCUMENTS

| JP | 2006-506128 | 2/2006 |
| JP | 2013-526337 | 6/2013 |

(Continued)

OTHER PUBLICATIONS

Examination Report for Australian Application No. 2018294240 dated Apr. 16, 2020, 4 pages.
(Continued)

*Primary Examiner* — Aaron F Roane
(74) *Attorney, Agent, or Firm* — Womble Bond Dickinson (US) LLP

(57) ABSTRACT

A robotic surgical system may include an actuator including a plurality of linearly displaceable drive members, where at least one drive member actuates at least one degree of freedom of a surgical instrument, and a sterile adapter interposed between the actuator and the surgical instrument. The sterile adapter includes a flexible barrier and a plurality of extensible covers integrally formed with the flexible barrier, and the plurality of extensible covers are arranged to receive the plurality of drive members. In some variations, the system may include an interlocked arrangement coupling the actuator and the surgical instrument across the sterile adapter, the interlocked arrangement urging the actuator and the surgical instrument together when the actuator actuates the at least one degree of freedom of the surgical instrument.

19 Claims, 17 Drawing Sheets

(52) U.S. Cl.
CPC ............... *A61B 2017/00477* (2013.01); *A61B 2017/00862* (2013.01); *A61B 2034/305* (2016.02)

(58) Field of Classification Search
USPC .......................................................... 606/1
See application file for complete search history.

(56) References Cited

U.S. PATENT DOCUMENTS

| | | | |
|---|---|---|---|
| 7,357,774 | B2 | 4/2008 | Cooper |
| 7,666,191 | B2 | 2/2010 | Orban et al. |
| 7,699,855 | B2 | 4/2010 | Anderson et al. |
| 7,727,244 | B2 | 6/2010 | Orban et al. |
| 7,819,885 | B2 | 10/2010 | Cooper |
| 7,947,050 | B2 | 5/2011 | Lee et al. |
| 8,105,338 | B2 | 1/2012 | Anderson et al. |
| 8,202,278 | B2 | 6/2012 | Orban et al. |
| 8,206,406 | B2 | 6/2012 | Orban et al. |
| 8,672,922 | B2 | 3/2014 | Loh et al. |
| 9,320,568 | B2 | 4/2016 | Orban et al. |
| 2015/0173840 | A1 | 6/2015 | Lohmeier |
| 2016/0184037 | A1 | 6/2016 | Cooper et al. |
| 2017/0020615 | A1 | 1/2017 | Koenig et al. |

FOREIGN PATENT DOCUMENTS

| | | |
|---|---|---|
| WO | 2011143024 | 11/2011 |
| WO | WO2011143024 A1 | 11/2011 |
| WO | WO2017015599 A1 | 1/2017 |

OTHER PUBLICATIONS

International Preliminary Report on Patentability for International Application No. PCT/US2018/040142 dated Jan. 9, 2020, 9 pages.
PCT Search Report and Written Opinion dated Oct. 11, 2018, for related PCT Appln. No. PCT/US2018/040142 7 Pages.
Notice of Reasons for Rejection for Japanese Application No. 2019-566690 dated Jan. 12, 2021, 12 pages.
Examiner's Report for Canadian Application No. 3,066,527 dated Mar. 31, 2021, 4 pages.

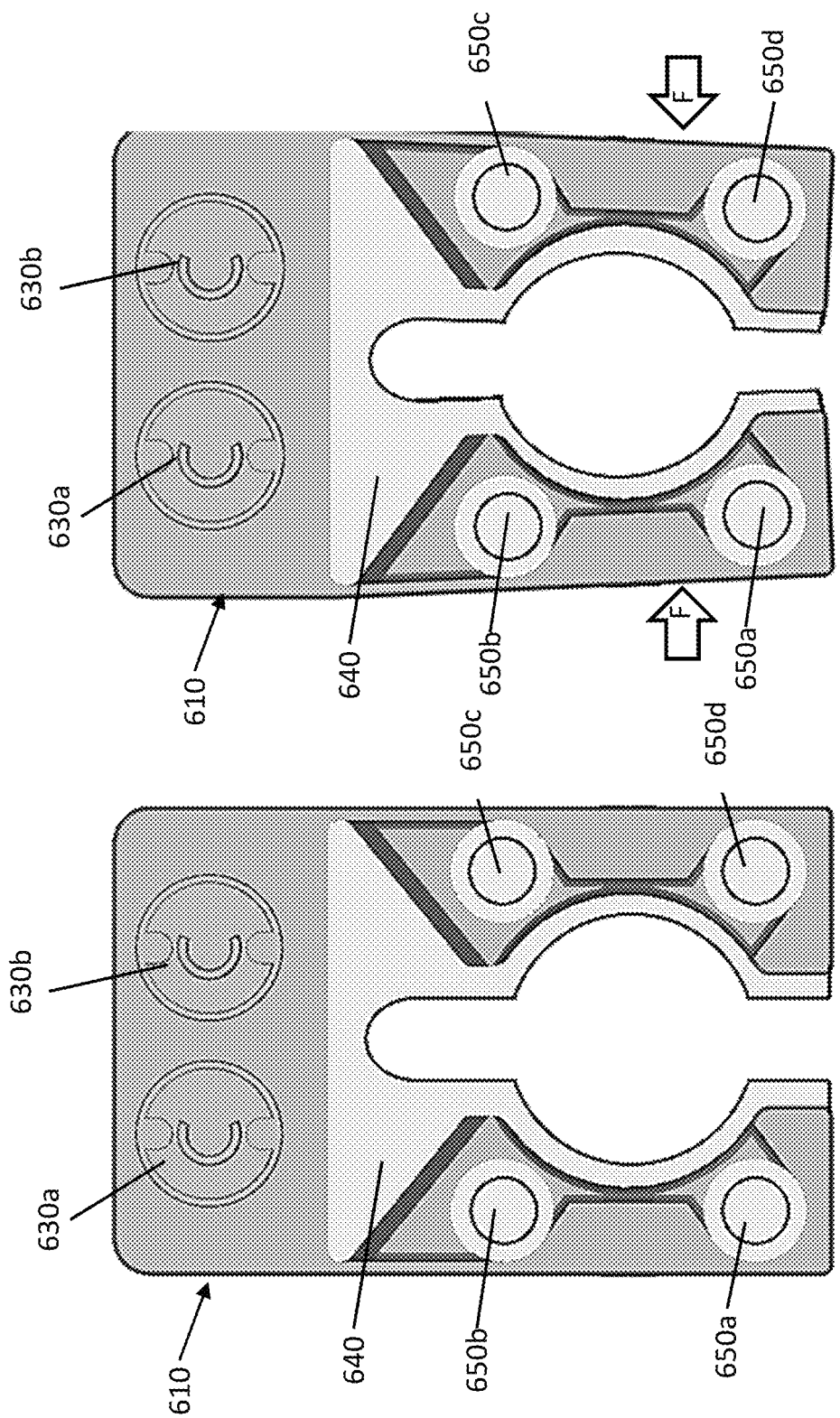

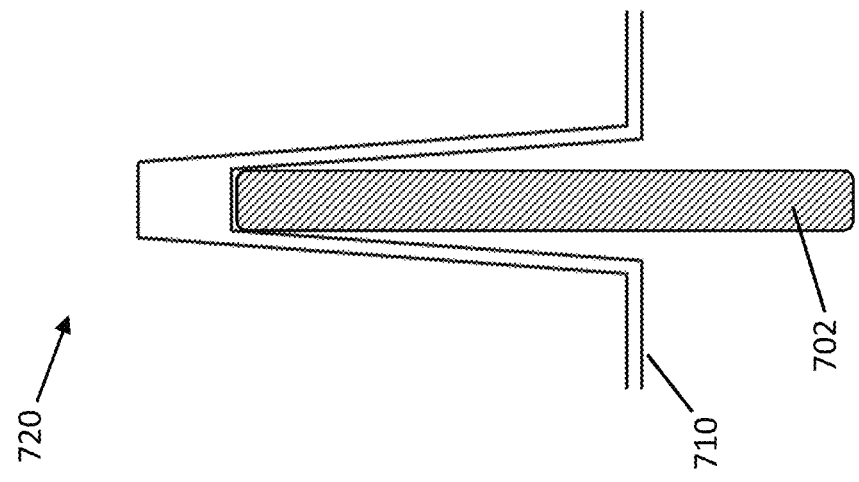
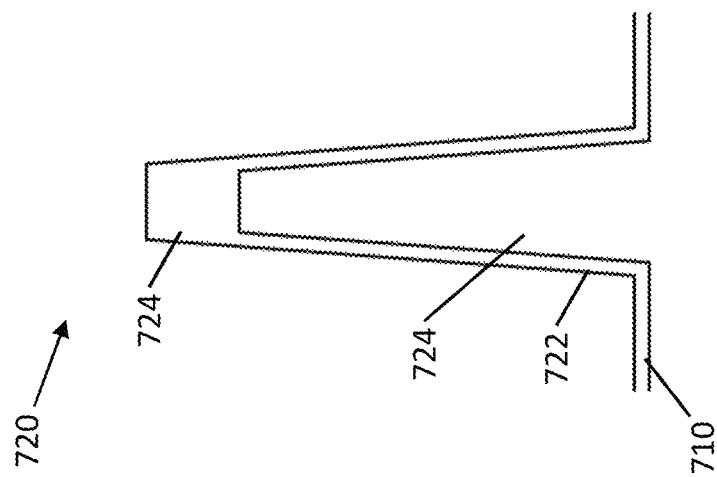
FIG. 8B
FIG. 8A

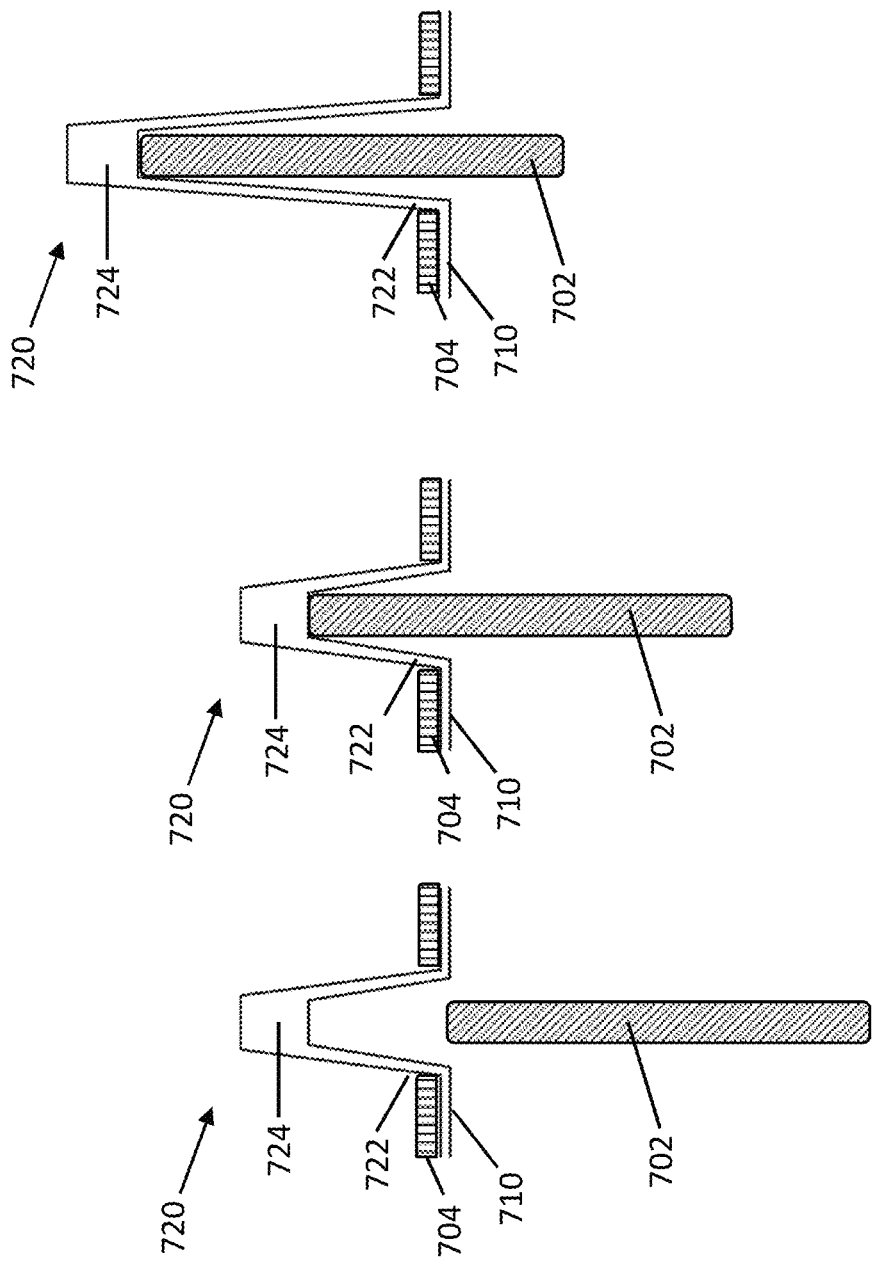

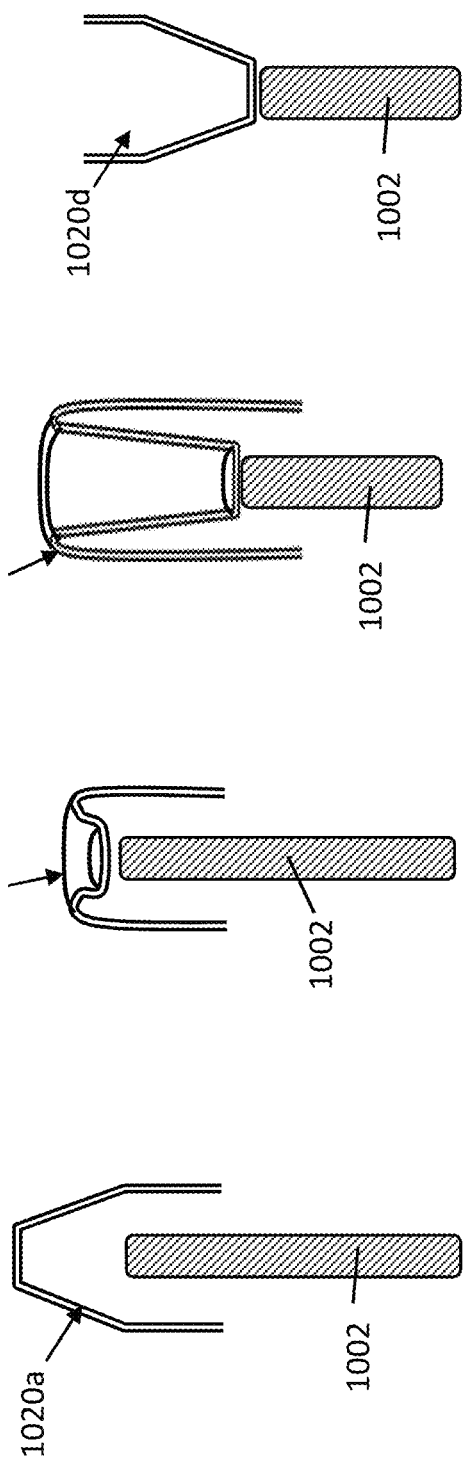
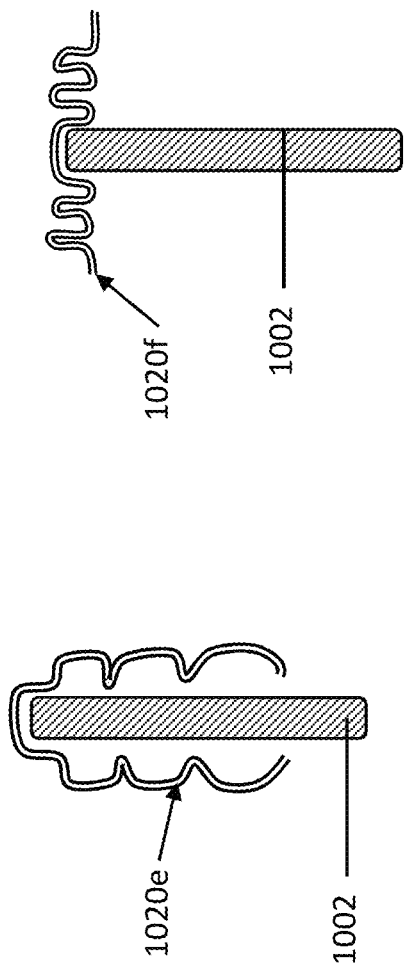

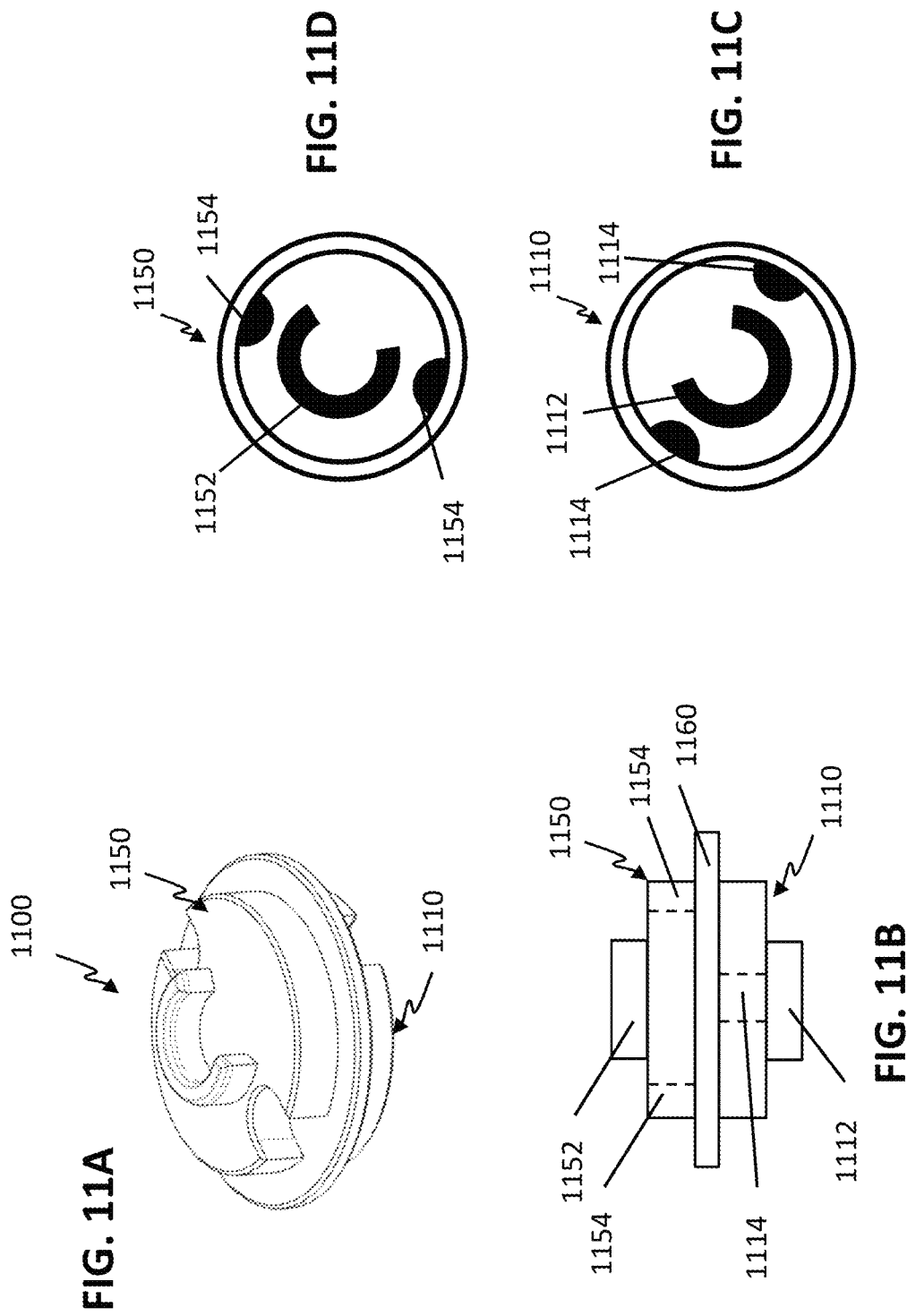

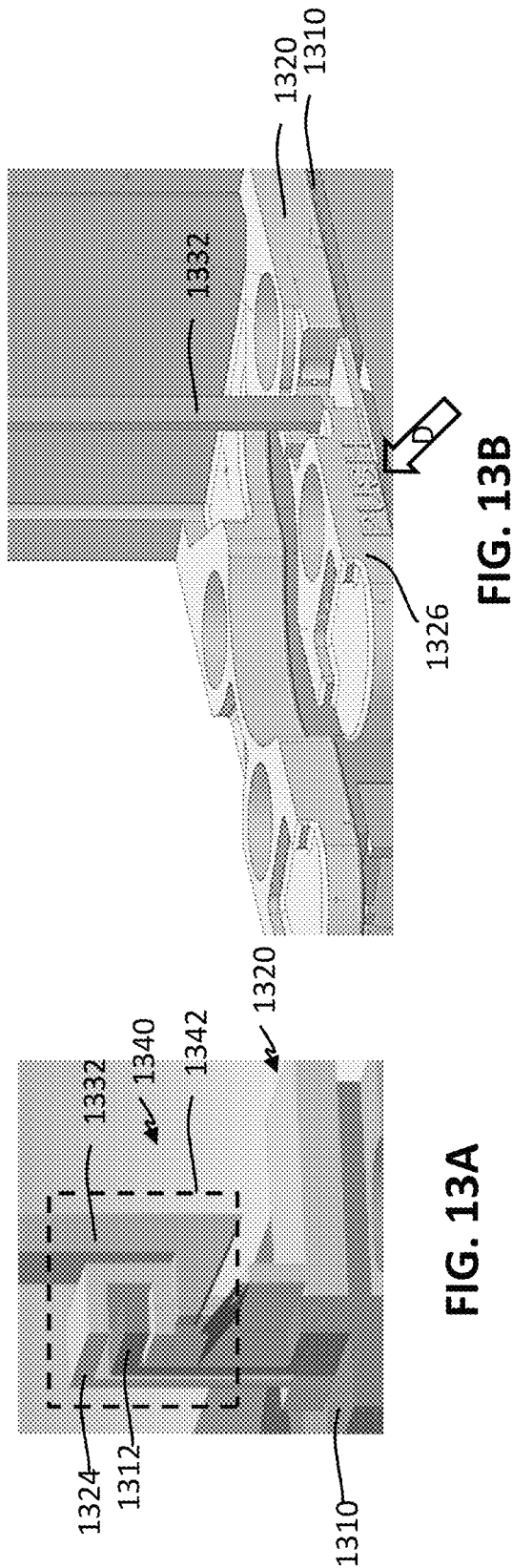

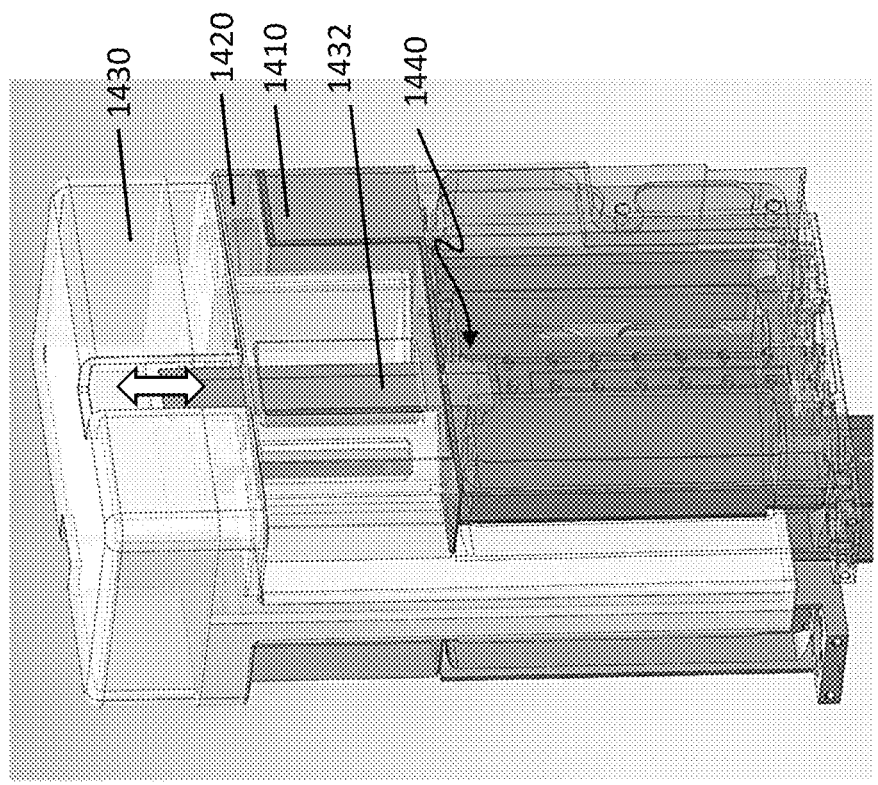

STERILE ADAPTER FOR A LINEARLY-ACTUATING INSTRUMENT DRIVER

CROSS-REFERENCE AND RELATED APPLICATIONS

This application claims priority to U.S. Provisional Patent Application Ser. No. 62/526,871, filed on Jun. 29, 2017, which is hereby incorporated by reference in its entirety.

TECHNICAL FIELD

This invention relates generally to robotic surgical systems, and more specifically to new and useful sterile adapters for creating a sterile barrier around portions of a robotic surgical system.

BACKGROUND

Minimally-invasive surgery (MIS), such as laparoscopic surgery, involves techniques intended to reduce tissue damage during a surgical procedure. For instance, laparoscopic procedures typically involve creating a number of small incisions in the patient (e.g., in the abdomen), and introducing one or more instruments (e.g., one or more tools, at least one camera, etc.) through the incisions into the patient. The surgical procedures are then performed by using the introduced tools, with the visualization aid provided by the camera. Generally, MIS provides multiple benefits, such as reduced patient scarring, less patient pain, shorter patient recovery periods, and lower medical treatment costs associated with patient recovery.

MIS may be performed with non-robotic or robotic systems. Conventional robotic systems, which may include robotic arms for manipulating instruments based on commands from an operator, may provide many benefits of MIS while reducing demands on the surgeon. Control of such robotic systems may require control inputs from a user (e.g., surgeon or other operator) via one or more user interface devices that translate manipulations or commands from the user into control of the robotic system. For example, in response to user commands, an instrument driver having one or more motors may actuate one or more degrees of freedom of a surgical instrument when the surgical instrument is positioned at a surgical site in the patient.

Similar to traditional surgical procedures, it is important to maintain a sterile environment in the surgical field during robotic MIS. However, various components (e.g., motors, encoders, sensors, etc.) of the instrument driver and other aspects of the robotic surgical system cannot practically be sterilized using conventional sterilization methods such as heat. One solution to maintain sterility is to provide a sterile barrier between the instrument driver (and other system components that may appear in the surgical field such as robotic arms, etc.) and the surgical instrument, thereby providing a "non-sterile" side for the instrument driver and a "sterile" side for the surgical instrument. However, the sterile barrier must not interfere with how the instrument driver actuates the surgical tool. Thus, it is desirable to have new and improved sterile adapters in a sterile barrier in a robotic surgical system.

SUMMARY

Generally, in some variations, a robotic surgical system may include an actuator comprising a plurality of linearly displaceable drive members, where at least one drive member actuates at least one degree of freedom of a surgical instrument, and a sterile adapter interposed between the actuator and the surgical instrument. The sterile adapter may include a flexible barrier and a plurality of extensible covers integrally formed with the flexible barrier, and the plurality of extensible covers may be arranged to receive the plurality of drive members. Additionally, the system may include a sterile drape coupled to the sterile adapter (e.g., attached around a periphery of the sterile adapter).

In some variations, the sterile adapter may include a frame coupled to the flexible barrier. The flexible barrier may, for example, be integrally formed with the flexible barrier (e.g., co-injection molded). For example, the frame, the flexible barrier, and the plurality of extensible covers may be integrally formed as one piece.

In some variations, the actuator may include an instrument mount interface and the flexible barrier may conform to the instrument mount interface. For example, the instrument mount interface may include a cavity that is configured to receive a portion of the surgical instrument, and the flexible barrier may conform to the cavity between the instrument mount interface and the portion of the surgical instrument. In some variations, the engagement of the surgical instrument with the instrument mount interface (e.g., across a sterile adapter) may substantially prevent decoupling of the actuator and the sterile adapter. For example, the presence of the surgical instrument in the cavity may substantially block or otherwise prevent manipulation of the sterile adapter that would otherwise facilitate decoupling of the sterile adapter from the instrument mount interface.

At least one of the extensible covers may transition between a rest state and a fully extended state in accordance with linear displacement of a drive member received in the at least one extensible cover. For example, the length of the extensible cover may generally vary with linear movement (extension and retraction) of the drive member received within the extensible cover. The cover length change and linear movement may, for example, vary linearly with generally 1:1 correspondence, or alternatively in any suitable relationship. In some variations, the length of the extensible cover in the rest state may be between about 40% and about 60% of the length of the extensible cover in the fully extended state, or about 50% of the length of the extensible cover in the fully extended state.

One or more of the extensible covers may include an elastomeric material such as silicone. At least some of the extensible covers may be reinforced at an enclosed distal end of the cover (e.g., to resist breakage as the drive member is actuated against the extensible cover). For example, in some variations of extensible covers, the distal end may be thicker than the side wall of the extensible cover. As another example, the distal end may include a material that is harder and/or tougher than the side wall of the extensible member.

Furthermore, generally, in some variations, a robotic surgical system may include an actuator including at least one linearly displaceable drive member, a surgical instrument having at least one degree of freedom actuated by the at least one drive member, a sterile adapter interposed between the actuator and the surgical instrument, and an interlocked arrangement coupling the actuator and the surgical instrument across the sterile adapter. The interlocked arrangement may urge the actuator and the surgical instrument together when the actuator actuates the at least one degree of freedom of the surgical instrument. For example, the interlocked arrangement may be configured such that when the actuator actuates the at least one degree of freedom and causes a reaction force (e.g., with a tendency to separate the actuator and the surgical instrument), the interlocked arrangement may leverage the reaction force into a compression force that tends to urge the actuator and surgical instrument together.

The interlocked arrangement may include a first portion coupled to the actuator and a second portion coupled to the surgical instrument. For example, the first portion may include a first interlocking member and the second portion may include a second interlocking member configured to engage with the first interlocking member to thereby form at least part of the interlocked arrangement. In some variations, one or both of the first and second interlocking members may include a latch (e.g., serve as a latch). For example, in some variations, the latch may be pivotable and operatively coupled to a handle, where the handle is manipulable for releasably coupling the actuator and the surgical instrument.

A method may include coupling a sterile adapter to an actuator including at least one linearly displaceable drive member, coupling a surgical instrument to the actuator across the sterile adapter via an interlocked arrangement such that the sterile adapter is interposed between the actuator and the surgical instrument, and controlling the drive member to actuate at least one degree of freedom of the surgical instrument. When the drive member is actuated in such a manner, the interlocked arrangement may urge the actuator and the surgical instrument together.

The method may further include decoupling the surgical instrument from the actuator at least in part by disengaging the interlocked arrangement. For example, decoupling the surgical instrument from the actuator may include maneuvering a handle coupled to the surgical instrument away from the actuator and the sterile adapter, thereby separating first and second portions of the interlocked arrangement (e.g., where the first portion is coupled to the actuator and the second portion is coupled to the surgical instrument). In this example, disengaging the interlocked arrangement may include, for example, pulling the handle away from the actuator and sterile adapter in a complementary or intuitive manner that is reflective of an intuitive motion for separating the surgical instrument from the actuator and sterile adapter.

BRIEF DESCRIPTION OF THE DRAWINGS

FIGS. 7A and 7B are top views of a frame in an exemplary variation of a sterile adapter, in flexed and unflexed configurations, respectively.

FIGS. 8A and 8B are schematic illustrations of an extensible cover in an exemplary variation of a sterile adapter.

FIGS. 9A, 9B, and 9C are schematic illustrations of the extensible cover depicted in FIGS. 8A and 8B, in a fully rested position with a driving member fully retracted, in a fully rested position with a driving member partially extended, and in a fully extended position with a driving member fully extended, respectively.

FIGS. 10A-10F are cross-sectional views of different variations of an extensible cover.

FIG. 11A is a perspective view of an exemplary variation of a rotatable coupler. FIGS. 11B, 11C, and 11D are side, bottom, and top views of the rotatable coupler depicted in FIG. 11A.

FIGS. 13A and 13B are a detailed view and a perspective view, respectively, of another exemplary variation of an interlocked arrangement.

FIG. 14 is a perspective view of another exemplary variation of an interlocked arrangement.

DETAILED DESCRIPTION

Examples of various aspects and variations of the invention are described herein and illustrated in the accompanying drawings. The following description is not intended to limit the invention to these embodiments, but rather to enable a person skilled in the art to make and use this invention.

System Overview

Figure 1:
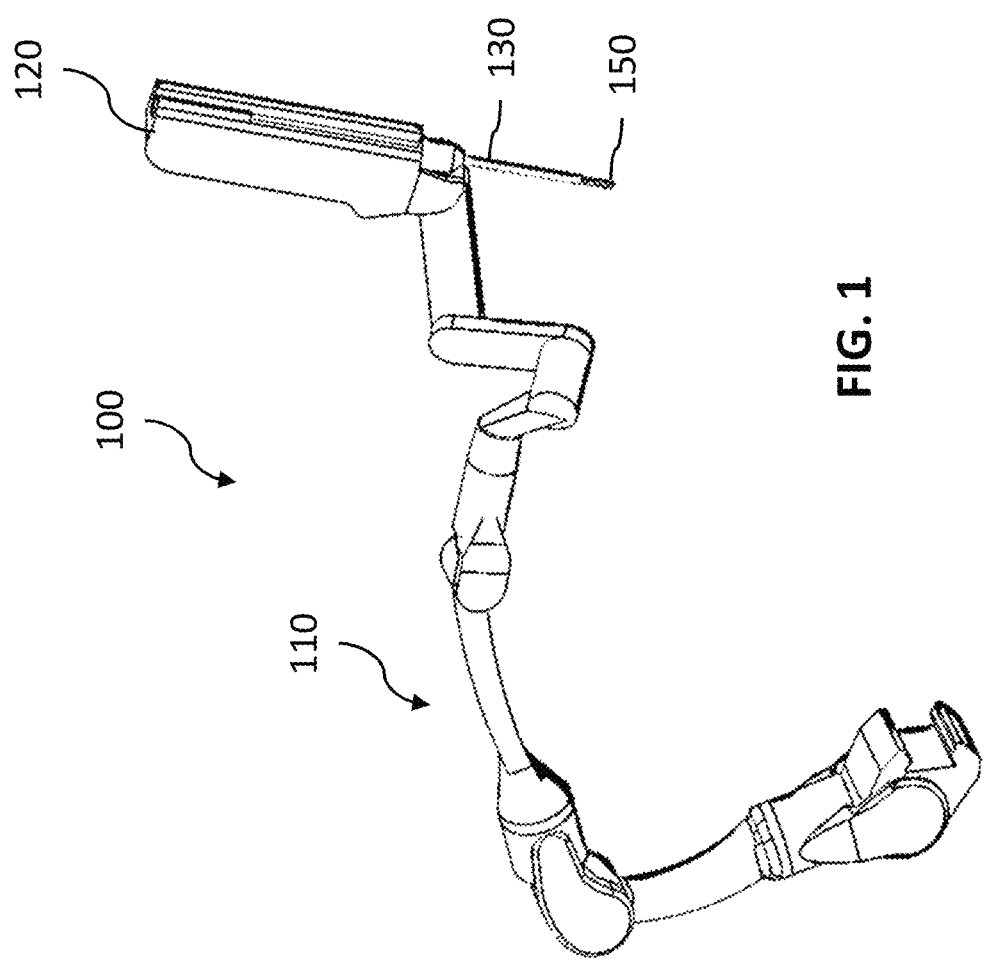
FIG. 1 is a schematic illustration of one exemplary variation of an instrument driver on a robotic arm manipulator.

Generally, a robotic or robotic-assisted surgical system (e.g., to enable a minimally-invasive surgical procedure) may include one or more robotic arms for manipulating surgical instruments, such as during minimally-invasive surgery. For example, as shown in the exemplary schematic of FIG. 1, a robotic surgical system 100 may include a robotic arm 110 and an instrument driver 120 (actuator) generally attached to a distal end of the robotic arm 110. A cannula 130 coupled to the instrument driver 120 may telescopically receive a surgical instrument 150. Furthermore, the robotic arm 110 may include a plurality of links that are actuated so as to position and orient the instrument driver 120.

For use in a surgical procedure, the robotic arm 110 may be mounted to an operating table on which a patient lies (or on a cart, ceiling, sidewall, etc. near the patient). To create a port for enabling introduction of a surgical instrument into the patient, a trocar assembly (typically a cannula 130 and obturator) may be at least partially inserted into the patient through an incision or entry point in the patient (e.g., in the abdominal wall). The cannula 130 may be coupled to the instrument driver 120, and the instrument 150 may be coupled to the instrument driver 120 such that at least a portion (e.g., instrument shaft) passes through the cannula and into the patient. The instrument 150 may have an end effector disposed at the distal end of the instrument shaft, and the instrument driver 120 may further be controlled to position and/or actuate one or more degrees of freedom of the instrument 150 to perform various tasks during a surgical procedure (e.g., cutting, grasping, etc.) in accordance with the particular kind of end effector. Additionally, the instrument 150 may be withdrawn from the port and decoupled from the instrument driver 120 to exchange with another instrument, such as another instrument having an end effector with different functionality.

Figure 2:
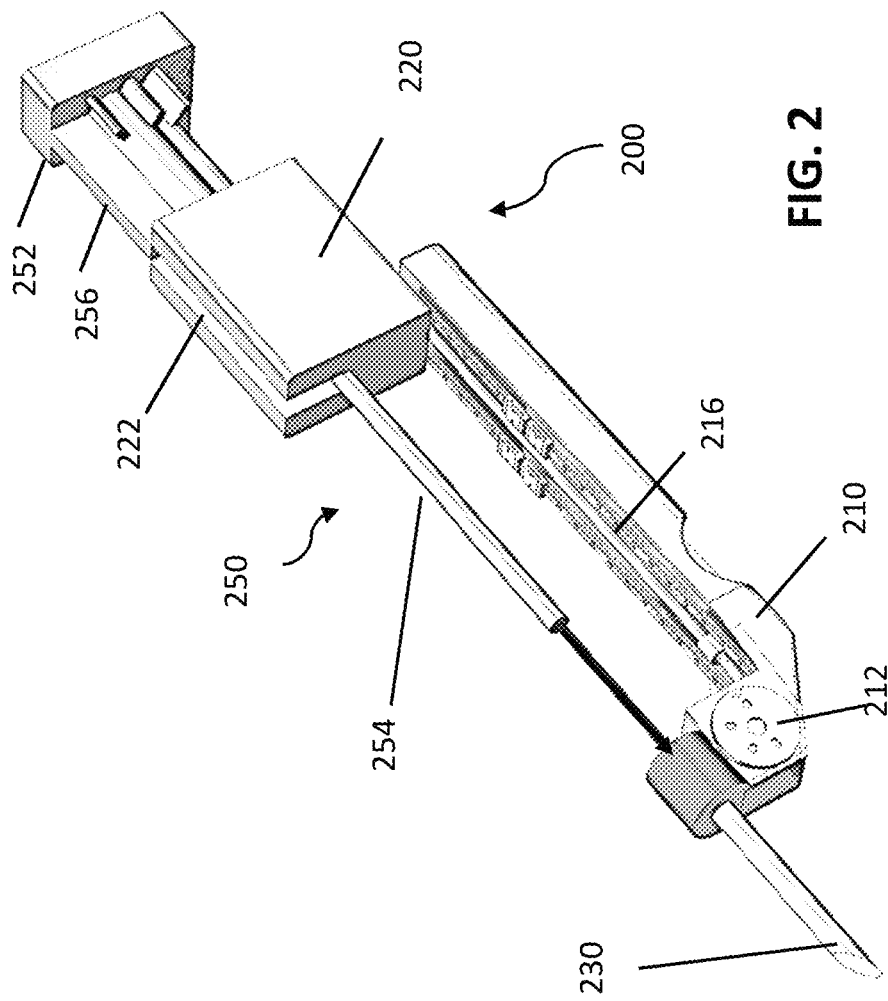
FIG. 2 is a perspective view of an exemplary variation of an instrument driver.

FIG. 2 illustrates one exemplary variation of an instrument driver 200. In this variation, the instrument driver 200 includes an elongated base 210 including a longitudinal track 216 (e.g., linear bearings) and a carriage 220 which is slidingly engaged with the longitudinal track 216. The base 210 may be configured to couple (e.g., at interface 212) to a distal end of a robotic arm such that articulation of the robotic arm positions and/or orients the instrument driver 200 in space. Additionally, the carriage may be configured to receive an instrument base 252 having an instrument shaft 254 extending from the instrument base 252 and further having an end effector disposed at a distal end of the instrument shaft. Generally, the instrument carriage 220 may be actuated along the longitudinal track 216 (along the base 210) to axially position the instrument shaft 254 within the cannula 230 and thus enable positioning of the end effector within a surgical workspace within the patient.

Generally, the carriage 220 may additionally be configured to orient and/or actuate the end effector of the surgical instrument 250, and/or to manipulate one or more degrees of freedom of the surgical instrument. For example, the carriage 220 may enable rotation of the instrument shaft around a longitudinal instrument axis, thereby rotating the end effector of the instrument about the longitudinal instrument axis. Additionally or alternatively, the carriage 220 may actuate a wrist joint of the end effector and/or one or more specific functionalities of the end effector (e.g., actuate a jaw or blade).

Figure 4:
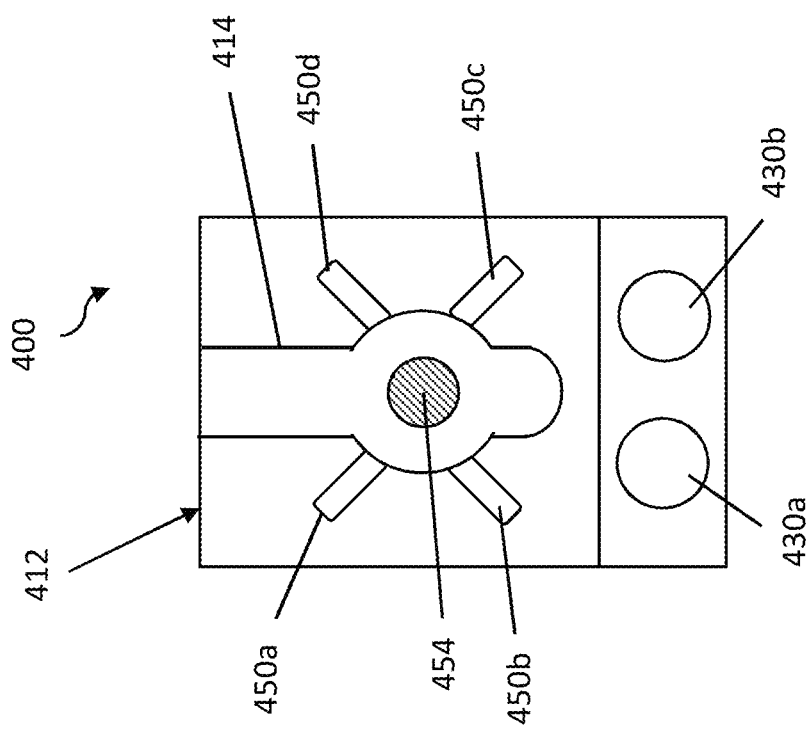
FIG. 4 is a schematic illustration of an instrument base of an exemplary variation of a surgical instrument.
Figure 3:
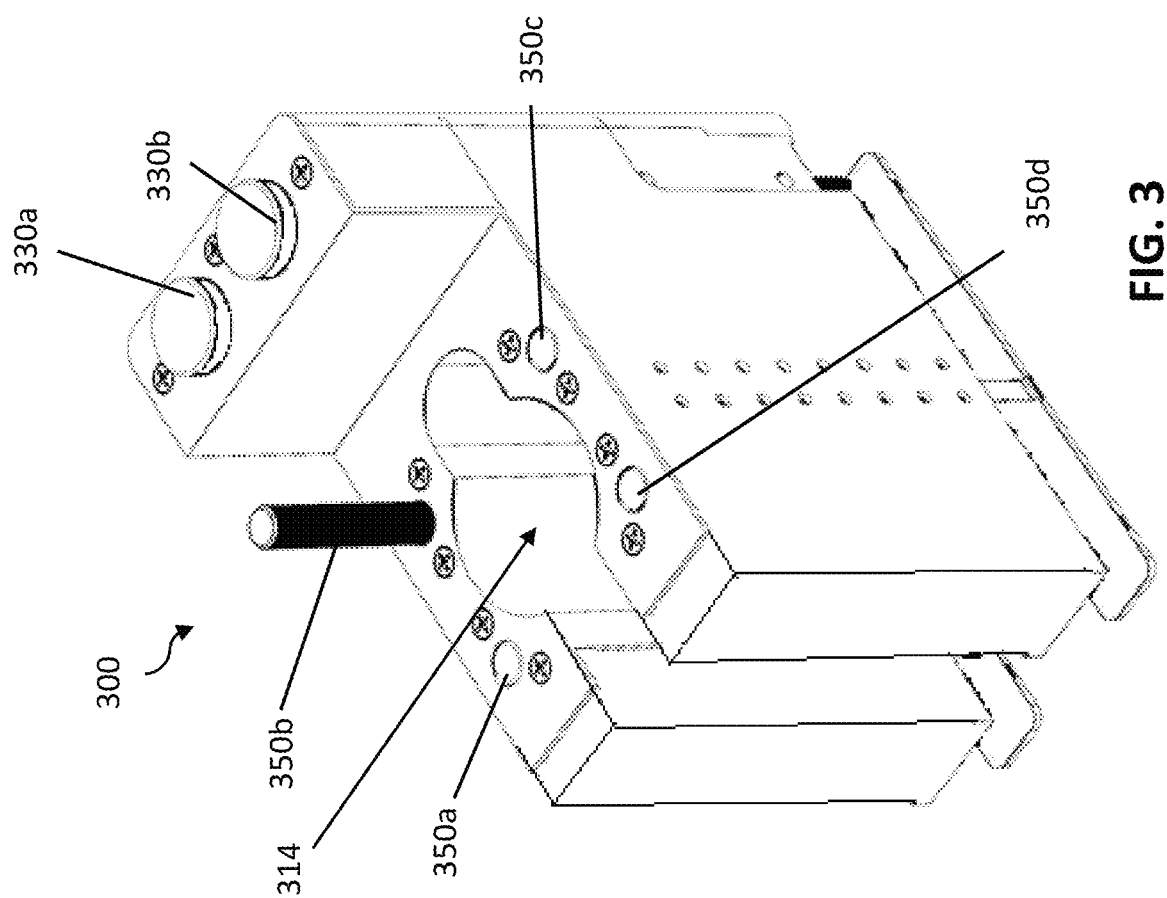
FIG. 3 is a schematic illustration of an exemplary variation of an instrument driver with a sterile adapter.

The carriage may include an instrument-receiving interface configured to couple to a surgical instrument, and the carriage and/or the surgical instrument may include features for enabling engagement and/or alignment. For example, as shown in FIG. 2, the carriage 220 may include an instrument mount interface including a longitudinal slot 222 (or cavity or other receptacle, etc.) for engaging an alignment projection 256 of the surgical instrument base 252. The engagement of the slot 222 and the alignment projection 256 may help secure coupling between the carriage and the surgical instrument and/or align actuated drives of the carriage with drive inputs of the surgical instrument (described in further detail below). As another example, as shown in FIGS. 3 and 4, a carriage 300 may include an instrument mount interface including a slot 314 for engaging and/or aligning with an alignment projection 414 of an instrument base 412. Slot 314 may, in some variations, include a generally circular region configured to complementarily mate with a generally circular region of the alignment projection 414. An instrument shaft 454 may extend from the instrument base 412 to also pass through the generally circular region of slot 314 (and into a cannula, etc.).

The carriage may include different suitable configurations of actuated drives for manipulating one or more degrees of freedom of a surgical instrument. For example, the carriage may include at least one linear axis drive (linear output drive) and/or at least one rotary axis drive (rotary output drive). In the exemplary variation as shown in FIG. 3, the carriage 300 of an instrument driver may include one or more linearly displaceable drive members (e.g., drive members 350a, 350b, 350c, and 350d). Each drive member may be linearly displaceable throughout a range of motion between a retracted position (e.g., as illustrated by drive members 350a, 350c, and 350d) in which the drive member is generally in a relative proximal location, and an extended position (e.g., as illustrated by drive member 350b) in which the drive member is generally in a relative distal location. Although four drive members are depicted in FIG. 3 as arranged on the carriage in a bilaterally symmetric manner, it should be understood that a plurality of drive members may be arranged in any suitable arrangement, and include any suitable number of drive members. The drive members may be controlled with a suitable linear actuator, such as an assembly including a motor and a leadscrew (or ballscrew, etc.) arrangement, a gear arrangement, etc.

Each drive member, as the result of being driven linearly in extension and/or retraction along an axial direction by a linear actuator, may actuate at least one degree of freedom of a surgical instrument, such as by engaging a drive input of the surgical instrument. For example, as shown in FIG. 4, a surgical instrument base 412 of a surgical instrument 400 may include one or more linear drive inputs (e.g., 450a, 450b, 450c, and 450d), such as flaps, levers, receptacles, or other mechanisms for receiving corresponding linearly displaceable drive members and actuating one or more degrees of freedom through a system of cables, belts, or other suitable driving elements. In the exemplary variations shown in FIGS. 3 and 4, when the surgical instrument 400 is coupled to the carriage 300, a first drive member 350a may engage a first linear drive input 450a, a second drive member 350b may engage a second linear drive input 450b, a third drive member 350c may engage a third linear drive input 450c, and a fourth drive member 350d may engage a fourth linear drive input 450d. In some variations, at least some drive members may actuate a separate respective degree of freedom of the instrument. In some variations, at least some drive members may actuate a common or the same degree of freedom (e.g., actuate opposite directions of a particular movement, such as with antagonistic wire control).

Furthermore, the carriage may additionally or alternatively include one or more rotary axis drives (e.g., for rotating the instrument shaft around an instrument axis, or actuating another suitable degree of freedom of the instrument). For example, as shown in FIG. 3, the carriage 300 may include one or more rotary output drives (e.g., 330a and 330b) which may engage one or more rotary input drives on the surgical instrument 400, such as via coupling drive discs or other suitable driving mechanism. First rotary output drive 330a may engage a first rotary input drive 430a, and second rotary output drive 330b may engage a second rotary input drive 430b. Like the linear axis drives described above, in some variations, at least some rotary output drives may actuate a separate respective degree of freedom of the instrument, while in some variations, at least some rotary output drives may actuate a common degree of freedom (e.g., in an antagonistic manner).

Sterile Barrier

Figure 5:
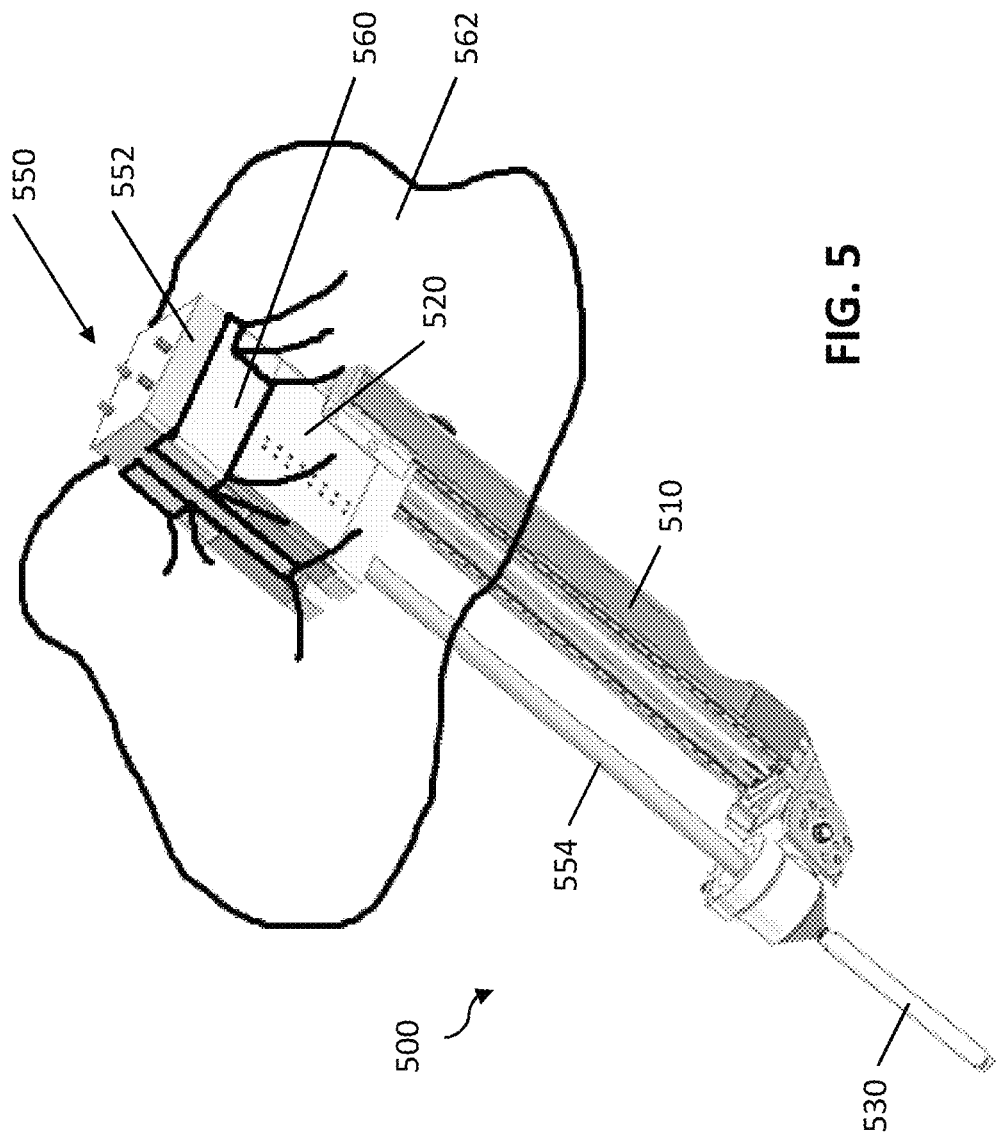
FIG. 5 is a schematic illustration of part of an exemplary variation of a robotic surgical system including an instrument driver, a surgical instrument, and a sterile barrier between the instrument driver and the surgical instrument.

In some variations, a robotic surgical system may further include a sterile barrier between non-sterile components (e.g., an instrument driver, a robotic arm, etc.) and sterile components (e.g., surgical instrument). As further described herein, such a sterile barrier may include a sterile adapter for being placed between an instrument driver and a surgical instrument, and a sterile drape coupled to the sterile adapter. For example, generally, in some variations, as shown in FIG. 5, a robotic surgical system may include an instrument driver 500 (actuator) with a carriage 520 and comprising a plurality of linearly displaceable drive members, in which at least one drive member actuates at least one degree of freedom of a surgical instrument. Similar to the carriage described above with reference to FIG. 2, the carriage 520 may travel along an elongated base 510 (similar to that described above with reference to FIG. 2), such that an instrument shaft 554 may correspondingly travel within a cannula 530. The robotic surgical system may further include a sterile adapter 560 interposed between the carriage 520 and the surgical instrument 550, and a sterile drape 562 may be coupled to the sterile adapter 560 (e.g., around the periphery of the sterile adapter 560) for providing an additional barrier between non-sterile components and sterile components.

Figure 6A:
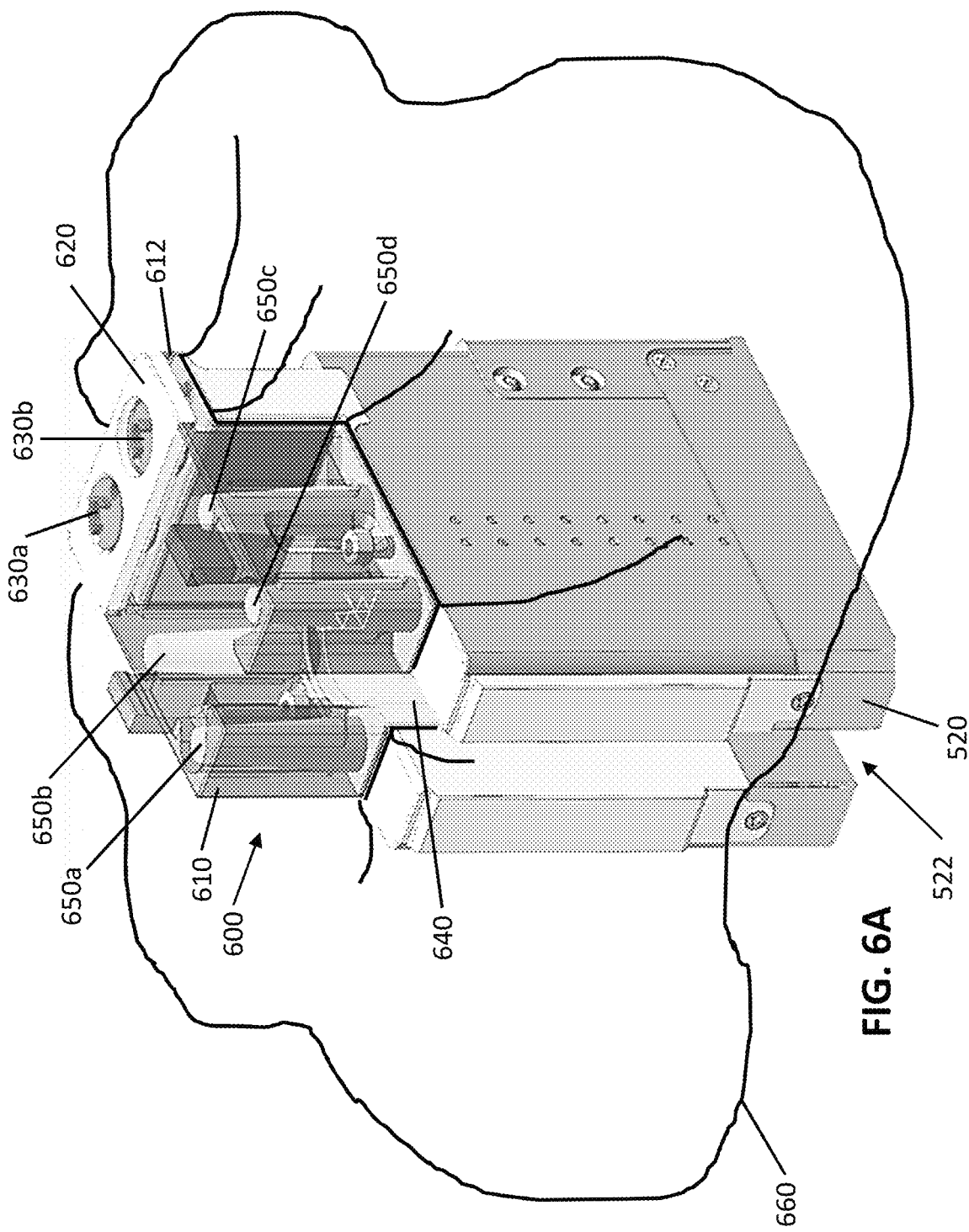
FIG. 6A is a perspective view of an exemplary variation of an instrument driver and sterile barrier with a sterile adapter and sterile drape.
Figure 6C:
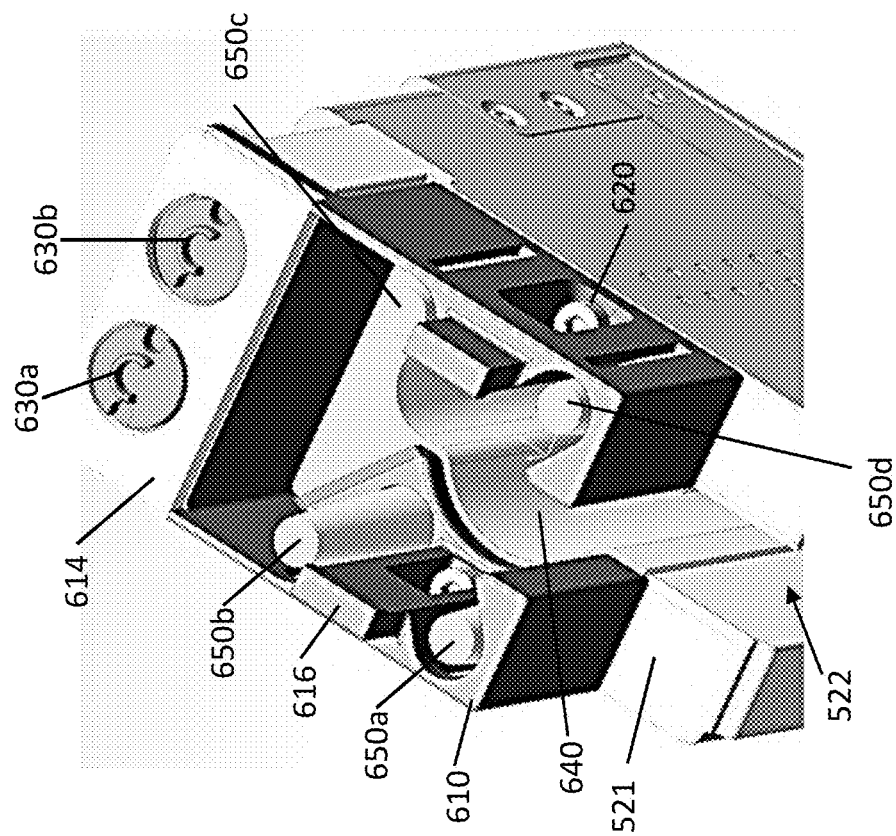
FIG. 6C is a top perspective view of the instrument driver and sterile adapter depicted in FIG. 6A.
Figure 6B:
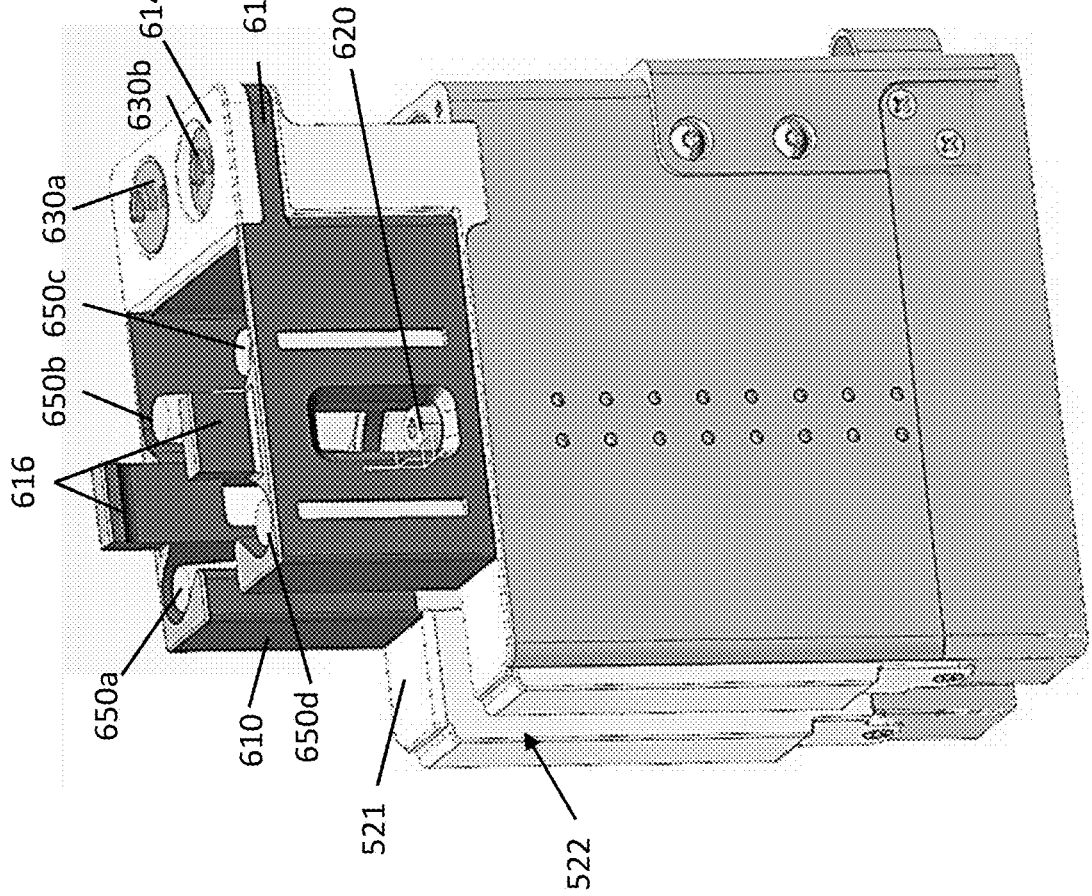
FIG. 6B is a perspective view of the instrument driver and sterile adapter depicted in FIG. 6A.
Figure 6E:
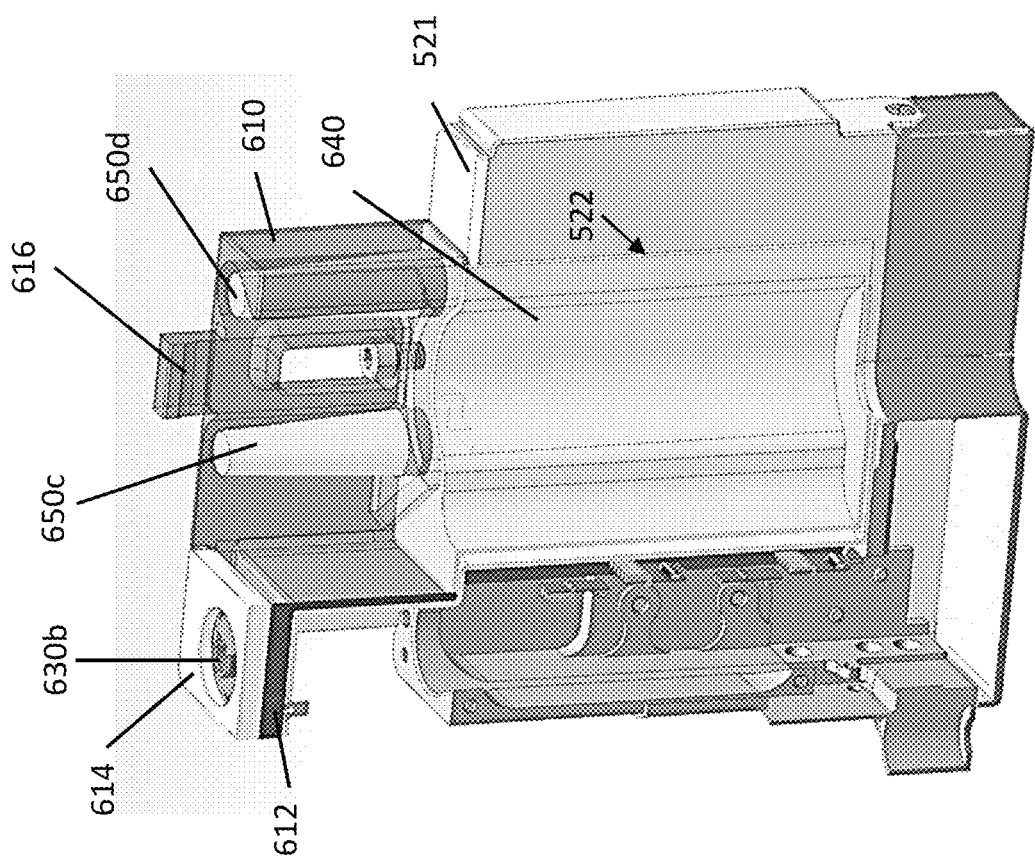
FIGS. 6D and 6E are cross-sectional views of the instrument driver and sterile adapter depicted in FIG. 6A.
Figure 6D:
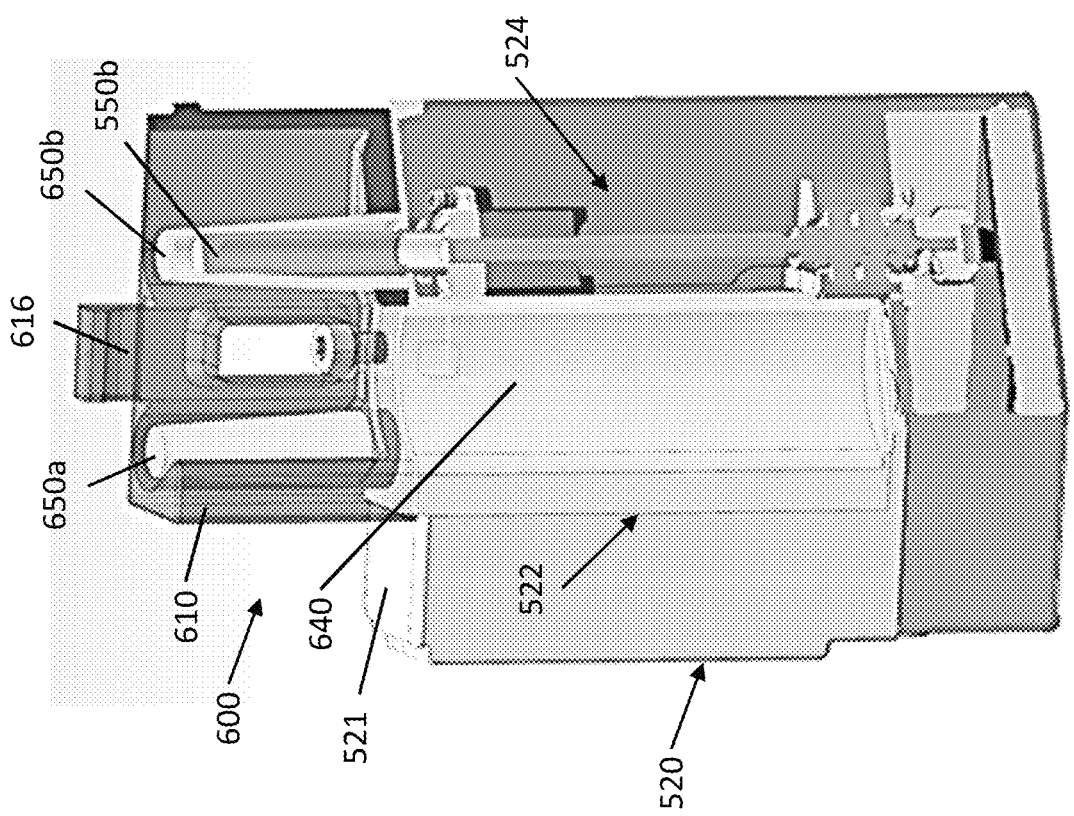

Generally, as shown in FIGS. 6A-6C, in some variations, a sterile adapter 600 may include a flexible barrier 640 and a plurality of extensible covers (e.g., 650a, 650b, 650c, and 650d) coupled to the flexible barrier 640. The plurality of extensible covers may be configured to communicate linear actuation from one or more linear drive members of the instrument driver to a surgical instrument, while helping to maintain a sterile barrier between the instrument driver and the surgical instrument. The flexible barrier 640 may, in some variations, be further coupled to a frame 610 providing further structural support to the flexible barrier 640. Each of the plurality of extensible covers may include an inner receptacle (e.g., lumen, channel, or other internal volume), and the plurality of extensible covers may be arranged to receive the plurality of drive members of a carriage 520 within their inner receptacles. For example, as shown in FIG. 6D, when the sterile adapter 600 is coupled to a carriage 520, the extensible cover 650b may be axially aligned with a corresponding drive member 550b so as to receive the drive member. As the drive member 550b is linearly displaced by the linear actuator 524 (e.g., a ballscrew assembly with a motor), the extensible cover 650b may transition between a rest state and an extended state in accordance with the movement of the drive member, as further described below.

In some variations, the sterile adapter 600 may include one or more rotatable couplers (e.g., coupler discs) configured to communicate torque from one or more rotary output drives of the instrument driver to a surgical instrument, while helping to maintain a sterile barrier between the instrument driver and the surgical instrument. An exemplary variation of rotatable couplers is described elsewhere herein.

In some variations, the sterile adapter may be configured to communicate electrical signals, such as for communication and/or power (e.g., for sensors, etc.), between the instrument driver and the surgical instrument. For example, at least a portion of the sterile adapter, such as the frame, flexible barrier, and/or one or more extensible covers, may include one or more conductive metal contacts for transferring electrical signals between the instrument driver and the surgical instrument. Such metal contacts may, in some variations, additionally or alternatively be used to signal to a controller and/or processor that the sterile adapter is coupled to the instrument driver and/or to a surgical instrument (in other variations, the instrument driver and/or sterile adapter may include any suitable one or more sensors to detect the coupling of the sterile adapter to the instrument driver and/or surgical instrument, such as a proximity sensor or a capacitive sensor). Additionally or alternatively, communication, power, and/or other signals may be wirelessly communicated (e.g., via Bluetooth or other wireless communication protocol) in any suitable manner.

In some variations, the sterile barrier may be sterilized during manufacturing and packaged in a sterile package to be used for a surgical procedure. For example, the sterile adapter and sterile drape may be coupled to one another as described herein, and together may be sterilized (e.g., with radiation, steam, ethylene oxide, etc.). The sterile barrier may, in some variations, be configured for single use. For example, the sterile barrier may be sterilized and packaged in a sterile package for shipping, storage, etc. that is opened for use during a surgical procedure. Following the surgical procedure, the sterile barrier may be disposed of. In other variations, the sterile barrier may be reusable (e.g., configured for multiple uses, such as a limited number of uses before disposal). For example, the sterile barrier may be sterilized before use in each surgical procedure in the manner described above (e.g., during manufacturing, between adjacent multiple uses, etc.). In some variations, a portion of the sterile barrier may be configured for multiple uses while another portion of the sterile barrier may be configured for single use only. For example, the sterile adapter may be configured for multiple uses and the sterile drape may be configured for single use, such that the sterile adapter may be sterilized and coupled to a new sterile drape before each surgical procedure (e.g., a used sterile drape may be swapped for a new, unused sterile drape). As another example, the sterile drape may be configured for multiple uses and the sterile adapter may be configured for single use, such that the sterile drape may be sterilized and coupled to a new sterile adapter before each surgical procedure (e.g., a used sterile adapter may be swapped for a new, unused sterile drape).

Frame

Generally, a frame of the sterile adapter may be configured to provide structural support to the sterile adapter. The frame may additionally or alternatively provide an interface for detachably coupling the sterile adapter to the instrument driver and/or the surgical instrument (e.g., a proximal base of the surgical instrument).

One exemplary variation of a frame 610 is shown as part of the sterile adapter 600 in FIGS. 6A-6E. As shown in, for example, FIGS. 6B and 6C, a first side of the frame 610 may be configured to couple to an instrument mount interface 521 of a carriage 520. For example, the frame 610 may couple to the mount interface 521 via one or more fasteners 620 (e.g., screw, bolt, etc.), a latch or other movable coupling mechanism, a snap fit or other interference fit, or in any other suitable manner. The first side of the frame 610 may be removably coupled to the instrument mount interface 521 to enable, for example, a current sterile adapter to be swapped for another sterile adapter (e.g., between surgical procedures) or for sterilization separate from the instrument driver. The first side of the frame 610 may, in some applications, be referred to as a non-sterile side of the frame 610, in that the first side of the frame 610 may be configured to couple to or otherwise interface with only non-sterile components of the robotic surgical system. Furthermore, a second side of the frame 610 (e.g., opposite the first side of the frame 610) may be configured to couple to a surgical instrument, such as a proximal instrument base of a surgical instrument with drive inputs. The second side of the frame 610 may, in some applications, be referred to a sterile side of the frame 610, in that the second side of the frame 610 may be configured to couple to or otherwise interface with only sterile components of the robotic surgical system or other sterile aspects of a surgical environment.

As shown in FIGS. 7A and 7B, in some variations, the frame 610 may include a generally "U"-shaped structure which may correspond to the shape of the instrument mount interface of the carriage. Such a structure may, for example, provide structural support for coupling the sterile adapter to the mount interface 521 of the carriage. Additionally, the legs of the "U"-shaped structure may be inwardly flexible and deformable toward a midline of the frame 610 (as illustrated in FIG. 7B). In variations in which coupling to the carriage is via a snap fit or other interference fit, this manner of flexible deformation may, for example, help facilitate installation and removal of the sterile adapter from the carriage 520, as described in further detail below. For example, other frame shapes (e.g., circular, elliptical, rectangular, etc.) may be suitable for coupling to other shapes of instrument mount interfaces.

In some variations, the frame 610 may generally encompass a workspace volume within which the drive members (e.g., 550b) travel. For example, as shown in FIGS. 6D and 6E, the frame 610 may have a height (e.g., measured as distance between the mount interface 521 and the instrument base of the surgical instrument) that is at least as tall as the difference between a fully recessed position of a drive member and a fully extended position of the drive member.

The frame 610 may include one or more openings for the extensible covers 650a, 650b, 650c, and 650d to be located. For example, as shown in FIGS. 6D and 6E, the frame 610 may include an opening for each extensible cover, where each extensible cover may pass through its respective opening of the frame 610. Furthermore, in some variations in which the carriage 520 includes one or more rotary output drives for actuating one or more rotary input drives of a surgical instrument, the frame 610 may include a mounting arrangement including one or more rotatable couplers, each rotatable coupler providing a sterile surface communicating torque from a rotary output drive to a rotary input drive. For example, as shown in FIG. 6B, the frame 610 may include a lower plate 612 and an upper plate 614, where at least one rotatable coupler (e.g., 630a, 630b) may be mounted between the lower plate 612 and the upper plate 614 in a manner that enables generally free rotation of the coupling disc but substantially prevents axial motion of the coupling disc. As described in further detail below, the coupling disc may have a first side (e.g., non-sterile side) configured to couple to a rotary output drive of the carriage, and a second side (e.g., sterile side) configured to couple to a rotary input drive, thereby communicating torque from the rotary output drive to the rotary input drive of the surgical instrument.

As shown in FIGS. 6A-6E, the frame may generally approximate a rectangular shape, but in other variations, the frame 610 may have any suitable shape (elliptical, circular, etc.). For example, the shape of the frame may correspond with the shape of a mount interface of the instrument driver, and/or the shape of the surgical instrument to which the sterile adapter is intended to couple. In some variations, the frame may be made at least partially of rigid or semi-rigid plastic with suitable flexibility for allowing sufficient deformation for facilitating coupling and decoupling of the sterile adapter and the instrument driver. For example, the frame may include polycarbonate (PC), acrylonitrile butadiene styrene (ABS), and/or a PC/ABS blend, and may or may not include fiberglass or carbon fiber filler (e.g., for strength). The frame may be injection molded, machined, 3D printed, or manufactured in any suitable process. In some variations, the frame may be co-injection molded with the material of the flexible barrier and/or extensible members (e.g., with a suitable mechanical interlock design).

Flexible Barrier

Generally, the sterile adapter may include a flexible barrier that is interposed between an instrument mount interface of an instrument driver (e.g., carriage) and a surgical instrument. In some variations, the flexible barrier may be compliant and form-fitting, or configured to conform to the instrument mount interface. For example, as shown in FIGS. 6C-6E, the flexible barrier 640 may generally conform to the "U"-shape of the instrument mount interface 521, including a slot or cavity 522 which complementarily receives a portion of a surgical instrument. In some variations, the flexible barrier may be molded (e.g., injection-molded) into a shape that approximates the geometry of the instrument mount interface. For example, as shown in FIGS. 6C-6E, the flexible barrier 640 may include a cavity portion configured to conform to the cavity 522 of the instrument mount interface.

The flexibility of the barrier 640 may, in some variations, help facilitate coupling and decoupling of the sterile adapter and the instrument driver. For example, the sterile adapter may have a flexed state as shown in FIG. 7B induced by one or more forces F by a user or other external source, and a generally unflexed state as shown in FIG. 7A in the absence of an external force. The flexed state of FIG. 7B may facilitate coupling of the sterile adapter and the instrument mount interface 521. In the flexed state, the legs of the frame's "U" shape may be bent inwards toward a midline, such that squeezing or laterally compressing the flexible barrier 640 makes it easier to insert the flexible barrier 640 into a cavity 522 (the position shown in FIGS. 6D and 6E). Once the forces F are released, the sterile adapter may revert to its unflexed state of FIG. 7A. In its unflexed state, the sterile adapter may configured to be securely coupled to the instrument mount interface 521, as frame 610 may have a generally "U"-shape and the flexible barrier 640 may be configured to conform to the cavity 522. As described above, when the sterile adapter is coupled to the instrument mount interface, a portion of a surgical instrument (e.g., an alignment projection) may engage with the cavity 522 across the flexible barrier 640. When removal of the sterile adapter is desired, the flexed state of the sterile adapter may again be induced by one or more forces F as shown in FIG. 7B to facilitate decoupling of the sterile adapter and the instrument mount interface 521. As described above, in the flexed state, the legs of the frame's "U" shape may be bent inwards toward a midline, such that the frame 610 decouples from the instrument mount interface 521 and laterally compresses the flexible barrier 640, thereby making it easier to remove the flexible barrier 640 from the cavity 522 and separate the sterile adapter from the instrument mount interface 521. It should be understood that advantageously, the presence of a surgical instrument engaged with the cavity 522 across the flexible barrier 640 also blocks or prevents deformation of the frame into its flexed state and accordingly, blocks or prevents removal of the sterile adapter from the instrument driver as long as the surgical instrument is engaged with the cavity 522. Thus, inadvertent removal of the sterile adapter from the surgical instrument may be substantially prevented when a surgical instrument is coupled to the instrument driver across the sterile adapter.

In some variations, the flexible barrier 640 is made of a flexible, durable material such as silicone. The flexible barrier 640 may have substantially uniform wall thickness, though in some variations different regions of the flexible barrier 640 may have different thicknesses. In some variations, the flexible barrier 640 may have a thickness generally at least between about 0.25 mm and 0.75 mm. For example, the flexible barrier 640 may have a thickness generally between about 1 mm and about 2 mm, and in some examples may have a thickness of at least 0.5 mm in some regions. Generally, the flexible barrier 640 may be injection molded, or formed in any suitable process. In some variations, the flexible barrier 640 may be co-injection molded with the frame.

Extensible Cover

The sterile adapter may include one or more extensible covers, each configured to receive a respective linearly displaceable drive member of the instrument driver. For example, as shown in FIG. 8A, an extensible cover 720 may include a proximal end 722, a distal covered end 724, and an inner channel 724. The proximal end 722 of the extensible cover 720 may be coupled to the flexible barrier 720 (e.g., similar to flexible barrier 640 described above), such as by being integrally formed with the flexible barrier 720 or coupled via ultrasonic welding, epoxy, or other suitable fasteners or processes. The distal end 724 may be closed to cover or terminate one end of the inner channel 724. As shown in FIG. 8B, the inner channel 724 of the extensible cover 720 may receive a drive member 702 of an instrument driver. Accordingly, the extensible cover 720 may form a barrier between the drive member 702 and other components on a non-sterile side of the sterile adapter, and elements on a sterile side of the sterile adapter.

At least one extensible cover may be configured to transition between a shorter rest state and a longer, fully extended state in accordance with linear displacement of the received drive member. For example, the extensible cover may be in its rest state when the received drive member is in its most retracted or proximal position, and the extensible cover may be in its fully extended state when the received drive member is in its most extended distal position, such that the length of the extensible cover generally changes with linear actuation of the drive member, so as to keep the drive member covered throughout its range of motion.

In some variations, at least one extensible cover may stretch elastically from the rest state to the fully extended state in response to a tensile load applied by an outwardly moving drive member, and subsequently elastically return to the rest state when the tensile load is released as the result of an inwardly moving drive member. For example, the extensible cover may be made of silicone, or another suitable flexible material that is injection molded or formed in any suitable manner. As shown in FIGS. 8A and 8B, an exemplary stretchable extensible cover 720 may have a generally frustoconical shape, with a taper extending from the proximal end 722 to the distal end 724. The wall thickness within the cover 720 may be generally uniform, or may vary throughout different portions of the cover (e.g. thicker near a proximal portion of the cover and thinner near a distal portion of the cover).

As another example, as shown in FIG. 10A, another exemplary stretchable extensible cover 1020a may include a generally cylindrical proximal portion and a generally frustoconical distal portion coupled to the proximal portion. One or both of the proximal portion and the distal portion may be extensible with linear displacement of a drive member 1002. The proximal and distal portions may be integrally formed (e.g., both made of silicone), or may be separate portions (e.g., separate materials, for example separate materials with different elasticities) that are coupled together through ultrasonic welding, etc. or other suitable process.

As yet another example, as shown in FIG. 10B, another exemplary stretchable extensible cover 1020a may include a generally cylindrical proximal portion and a deformable membrane coupled to the proximal portion. One or both of the proximal portion and the membrane may be extensible with linear displacement of a drive member 1002.

In some variations, the extensible cover may change length at least in part due to inversion of at least a portion of the cover. For example, as shown in FIG. 10C, an exemplary inverted cover 1020c may have a generally frustoconical shape in its rest state, with its narrower tapered end oriented proximally. The cover 1020c may be configured to invert with linear extension of a drive member 1002, such that when the drive member is in its fully extended state, the cover 1020 has its narrower tapered end oriented distally. The cover 1020c may be biased to revert to its rest state by default without external forces, such that when the drive member is in its fully retracted state, the cover 1020 returns to is uninverted state with its narrower tapered end oriented proximally. As another example, as shown in FIG. 10D, an exemplary inverted cover 1020d may include a generally cylindrical proximal portion and an inverted portion coupled to the proximal portion. Similar to the inverted cover 1020c shown in FIG. 10C, the cover 1020d may be configured to invert with linear extension of a drive member 1002 and return to its uninverted state when the drive member 1002 is in its fully retracted state. In some variations in which the at least a portion of the extensible cover inverts with linear displacement of the drive member, at least a portion of the cover may additionally stretch elastically to further allow for change in length of the cover.

In some variations, the extensible cover may change length at least in part due to one or more collapsible and extensible segments. For example, as shown in FIG. 10E, an exemplary bellows-like cover 1020e may include one or more laterally-oriented pleats (e.g., rings) forming serially-connected segments that enable the cover 1020e to longitudinally collapse and extend in accordance with linear displacement of a drive member 1002. As another example, as shown in FIG. 10F, an exemplary nesting cover 1020f may include one or more telescopic or nesting segments (e.g., concentric segments) that enable the cover 1020f to longitudinally collapse and extend in accordance with linear displacement of a drive member 1002. In other examples, an extensible cover may include segments that collapse and extend in a spiraling fashion, such as via helical pleats or folds, or spiral-cut telescopic segments.

The extensible cover may include an enclosed distal end (e.g., distal end cap). The distal end of the extensible cover may, in some variations, be reinforced (e.g., to resist tearing or other breakage). In one exemplary variation, as shown in FIGS. 8A and 8B, the distal end 724 of the extensible cover 720 may have a thickness greater than the side wall thickness of the cover. For example, the distal end 724 may be at least about 1.5 times, at least about 2 times, at least about 2.5 times, or at least about 3 times as thick as the side wall thickness of the cover. In another exemplary variation, the distal end 724 of the extensible cover may include a material that is tougher and/or harder than the flexible material of the rest of the cover 720. A second material of the distal end 724 may be coupled to the material of the rest of the cover 720 through co-injection molding, ultrasonic welding, epoxy, etc. or other suitable processes and/or mechanisms. For example, a suitable thermoplastic elastomer (e.g., MEDIPRENE, SANTOPRENE, thermoplastic vulcanizate (TPV)) and/or a suitable rigid or semi-rigid material (e.g., PC, ABS or PC/ABS blend) may be coupled to the distal end 724 of the extensible cover. Additionally and/or alternatively, the extensible cover may include geometric aspects that may reduce the risk of tearing or other breakage. For example, the corner junctures between the distal end 724 and the rest of the cover 720 may be radiused, which may, for example, help avoid stress concentrations. In variations in which the sterile adapter includes multiple extensible covers, some extensible covers may have different degrees of reinforcement. For example, some extensible covers may correspond to drive members moving through a greater range of linear motion, actuating more frequently-used degrees of freedom of surgical instrument, etc., and may thus expected to undergo larger strains and/or more cycles of extension and retraction. Such extensible covers may have distal ends that are more reinforced than that of other extensible covers in order withstand such increased demands.

In some variations, the length of the extensible cover may vary generally in a 1:1 correspondence or in a linear relationship with the drive member as the drive member moves throughout its linear range of motion. For example, the extensible cover may gradually increase in length continuously as the drive member moves from its most retracted position to its most extended position, with the drive member always in contact with the distal end of the extensible cover as the extensible cover increases in length.

In some variations, the length of the rest state of the extensible cover may vary with movement of the drive member in other suitable manners. For example, FIGS. 9A and 9B illustrate an exemplary rest state of one variation of an extensible cover 720, and FIG. 9C illustrates an exemplary fully extended state of the extensible cover 720. In FIG. 9A, the drive member 702 is in its most retracted position, but not yet in contact with the extensible cover 720 in its rest state. In FIG. 9B, the drive member 702 is in approximately a midpoint between its most retracted and most extended positions, and has barely made contact with the extensible cover 720 which is still in its rest state. Between the drive member positions shown in FIGS. 9A and 9B, the extensible cover 720 does not change in length. In FIG. 9C, the drive member 702 is in its fully extended position and the extensible cover is in its fully extended state. Between the drive member positions shown in FIGS. 9B and 9C, the drive member 702 pushes against the distal end 724 of the extensible cover, thereby causing a change in length of the extensible cover. Accordingly, as shown in FIGS. 9A-9C, the extensible cover 720 may provide a barrier for the drive member 702 throughout the range of motion of the drive member 702 while undergoing less overall strain, thereby reducing fatigue and risk of breakage as the drive member 702 moves (e.g., over repeated cycling). In some variations, the length of the extensible cover in the rest state may between about 25% and about 75% of the length of the extensible cover in the fully extended state, between about 40% and 60% of the length of the extensible cover in the fully extended state, or about 50% of the length of the extensible cover in the fully extended state.

As shown in FIGS. 9A-9C, the proximal end 722 of an extensible cover may be restrained at least in part by a portion of the frame 704. For example, the frame 704 may overlay a portion of the flexible barrier 710 and include an opening through which the extensible cover 720 passes. The overlaid portion of the flexible barrier 710 and proximal end 722 of the extensible cover 720 may be retained by virtue of the frame 704 coupled to the instrument driver. Accordingly, the proximal end of the cover 720 remains generally in the same location as the drive member 702 is actuated and pushes the cover 720, thereby allowing the length of the cover 720 to increase and/or decrease in accordance with the position of the drive member 702.

Rotatable Couplers

In some variations, the sterile adapter may include at least one rotatable coupler for communicating torque from a rotary output drive of an instrument driver to a rotary input drive of a surgical instrument, while maintaining a sterile barrier. For example, as shown in FIGS. 6A-6E and FIGS. 7A-7B, a sterile adapter may include rotatable couplers 630a and 630b. The rotatable couplers 630a and 630b may be mounted between a lower plate 612 and an upper plate 614 of the frame 610, in a manner that enables generally free rotation of the rotatable couplers 630a and 630b. Each rotatable coupler may include, for example, a body (e.g., disc) configured to be interposed between a rotary output drive of the instrument driver and a rotary input drive of the surgical instrument. A rotatable coupler may, in some variations, include a first face having a first arcuate feature configured to engage a rotary output drive of the instrument driver, and may further include a second face having a second arcuate feature configured to engage a rotary input drive of the surgical tool. The first and second arcuate features may have different arc lengths.

For example, as shown in FIGS. 11A and 11B, a rotatable coupler 1100 may include a first coupler portion 1110 configured to engage a rotary output drive of an instrument driver and a second coupler portion 1150 configured to engage a rotary input drive of a surgical instrument. First and second coupler portions 1110 and 1150 may be separate pieces that are coupled or affixed together (e.g., with epoxy or other suitable adhesive, thermal molding, press-fit of pins or other joining features, etc.). Alternatively, first and second coupler portions 1110 and 1150 may be integrally formed, such as through injection molding or being machined as one piece.

As shown in FIGS. 11B and 11C, the first coupler portion 1110 may include a first arcuate feature 1112 and one or more first drive features 1114. Similarly, as shown in FIGS. 11B and 11D, the second coupler portion 1150 may include a second arcuate feature 1152 and one or more second drive features 1154. Each of the first and second arcuate features 1112 and 1152 may, for example, include a circular segment. For example, the first and second arcuate features 1112 and 1114 may include circular segments (e.g., a "C"-shape) that are centered about an axis of rotation of the body of the rotatable coupler. In one variation, the first and second arcuate features 1112 and 1114 may include outward projections. For example, each outward projection may engage a corresponding arcuate channel on the rotary output drive of the instrument driver or the rotary input drive of the surgical instrument. However, it should be understood that additionally or alternatively, the first coupler portion 1110 and/or the second coupler portion 1150 may include an arcuate channel for engaging an outward projection on the rotary output drive of the instrument driver or the rotary input drive of the surgical instrument.

Figures 11E, 11F:
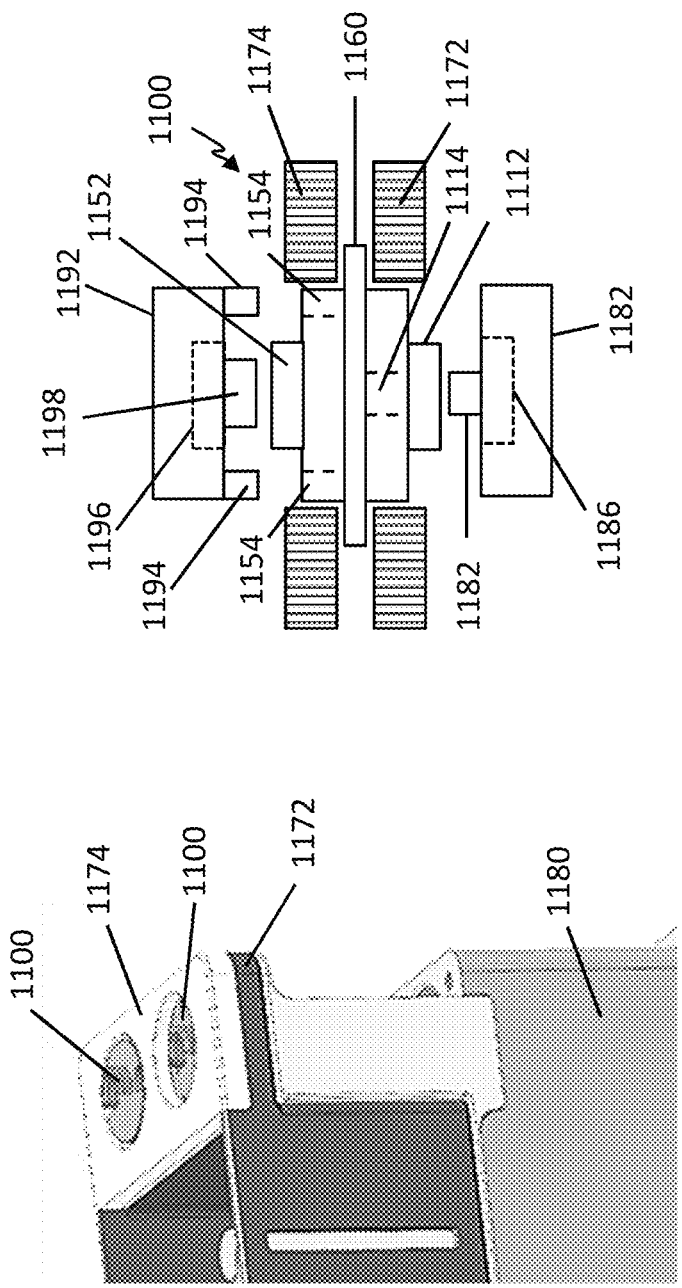
FIGS. 11E and 11F are perspective and cross-sectional views, respectively, of the rotatable coupler depicted in FIG. 11A mounted in a sterile adapter.

The arcuate features 1112 and 1152 may rotationally position the rotatable couplers for engagement with the instrument driver and the surgical instrument. In some variations, the arcuate features may at least partially function to ensure that there is a single rotational orientation of the rotatable coupler relative to a rotary output drive of an instrument driver and relative to a rotary input drive of a surgical instrument when the rotatable coupler is engaged with the instrument driver and the surgical instrument. For example, as shown in FIG. 11F, the first arcuate feature 1112 on the first coupler portion 1110 (e.g., having an instrument driver-facing side) may be configured to mate with a corresponding arcuate feature 1186 on a rotary output drive 1182 of an instrument driver. As an example, the first arcuate feature 1112 may include an arcuate outward projection sweeping a first angle, and the rotary output drive's arcuate feature 1186 may include an arcuate channel also sweeping the first angle and configured to receive the first arcuate feature 1112, such that there is only one relative rotational position in which the coupler arcuate feature 1112 and the rotary output drive's arcuate feature 1186 may mate and engage. As another example, the first arcuate feature 1112 may include an arcuate outward projection sweeping a first angle, and the rotary output drive's arcuate feature 1186 may include an arcuate outward projection sweeping a second angle, where the first and second angles sum to about 360 degrees. In this example, there is only one relative rotational position in which the coupler arcuate feature 1112 and the rotary output drive's arcuate feature 1186 may mate such that the rotatable coupler is fully seated against the instrument driver, with the arcuate outward projections 1112 and 1186 forming a full circle in combination. The second arcuate feature 1152 on the second coupler portion 1150 (e.g., with an instrument-facing side) may similarly be configured to mate with a corresponding arcuate feature 1196 on a rotary input drive 1192 of a surgical instrument.

The first coupler portion 1110 may further include one or more first drive features 1114 as shown in FIGS. 11B and 11C, and the second coupler portion 1150 may further include one or more second drive features 1154 as shown in FIGS. 11B and 11D. The drive features 1114 and 1154 may include, for example, pin holes or recesses (square, round, etc.) configured to engage with outward projecting drive pins on a rotary output drive of an instrument driver, and outward projecting drive pins on a rotary input drive of a surgical instrument. However, it should be understood that additionally or alternatively, the first coupler portion 1110 and/or the second coupler portion 1150 may include an outward projecting drive pin that engages a corresponding hole or recess on the rotary output drive of the instrument driver and on the rotary input drive of the surgical instrument. Furthermore, the drive features 1114 and 1154 may include chamfers to help guide engagement with corresponding drive features on the instrument driver and/or surgical instrument.

In one variation, the first coupler portion 1110 may include two drive features 1114 arranged about 180 degrees from one another, and the second coupler portion 1150 may include two drive features 1154 arranged about 180 degrees from one another. The set of the two drive features 1114 and the set of the two drive features 1154 may be rotationally offset by about 90 degrees (e.g., a first drive feature 1114 located at about 0 degrees, a second drive feature 1154 located at about 90 degrees, another first drive feature 1114 located at about 180 degrees, and another second drive feature 1154 located at about 270 degrees). For example, the first and second coupler portions 1110 and 1160 may be different instances of the same design (e.g., same size and shape) but rotated and affixed to one another back-to-back with a rotational offset of about 90 degrees. Such a rotational offset may, in some variations, permit and help compensate for axial misalignment between the output drive of the instrument driver and the input drive of the surgical instrument (e.g., operating similarly to a floating disc in an Oldham coupler). At least some of the drive features on the coupler 1100 may be elongated or slot-like, which may provide some tolerance accommodation and compensation for axial misalignment between the rotary output drive of the instrument driver and the rotary input drive of the surgical instrument. For example, the drive features 1114 on the first coupler portion 1110 may be somewhat elliptical to enable the coupler 1100 to translate around a circular drive pin on the instrument driver as the coupler 1100 rotates, while additionally the drive features 1154 on the second coupler portion 1150 may be somewhat elliptical to enable the coupler 1100 to translate around a circular drive pin on the surgical instrument. Thus, the drive features 1114 and 1154 may be able to compensate for at least some axial misalignment.

Furthermore, the first drive features 1114 may, in some variations, be about equidistant from the axis of rotation of the coupler 1100, and similarly the second drive features 1154 may be about equidistant from the axis of rotation of the coupler. In some variations, the first and second drive features 1114 and 1154 may be disposed near the edge or perimeter of the rotatable coupler 1100, so as to maximize torque transferred from the instrument driver to the surgical instrument through the coupler 1100.

As shown in FIG. 11F, the rotatable coupler 1100 may include an outer flange 1160 that helps retain and/or position the coupler 1100 within a frame of the sterile adapter (as also shown in FIG. 11E). For example, the outer flange 1160 may be disposed in a gap between a lower plate 1172 and an upper plate 1174, within enough clearance to permit the coupler 1100 to freely rotate between the lower and upper plates. The outer flange 1160 may be substantially continuous around the perimeter of the coupler 1100, though alternatively the coupler 1100 may include discrete segments (e.g., tabs) distributed around the perimeter of the coupler 1100.

In some variations, the rotatable couplers may include polycarbonate, ABS, other materials described above for the frame and/or plate assembly, or other suitable rigid material which may be injection molded, machined, extruded, stamped, 3D printed, or manufactured in any suitable manner.

Sterile Drape

In some variations, a sterile drape may be coupled to the sterile adapter to form a surrounding sterile barrier generally between non-sterile components (e.g., instrument driver, robotic arm, etc.) and sterile components and other portions of a sterile environment (e.g., surgical instrument, patient, etc.). For example, generally, as shown in FIG. 5, a sterile drape 562 may be coupled to a sterile adapter 560 for providing an additional barrier between non-sterile components and sterile components. The sterile drape 562 may be coupled around the periphery of the sterile adapter 560 (which is interposed between the carriage 520 of the instrument driver and the surgical instrument base 552).

In another exemplary variation, as shown in FIG. 6A, a sterile drape 660 may be coupled to the periphery of a sterile adapter 600 that is configured to be interposed between an instrument driver and a surgical instrument. In this variation, the sterile drape 660 may be coupled to the periphery of the frame 610 (e.g., bordering the lower plate 612 of the frame 610, bordering an edge or surface of the frame 610 that interfaces with the carriage 520) and/or the flexible barrier 640 (e.g., bordering an edge of surface of the flexible barrier 640 that conforms with the cavity 522 of the instrument driver). In other variations, the sterile drape 660 may additionally or alternatively border the upper plate 614, border an edge or surface of the frame 610 that interfaces with the surgical instrument base, and/or other suitable edges or surfaces of the sterile adapter for providing a barrier between the instrument driver (and other non-sterile components) and the surgical instrument (and other sterile components).

In some variations, the sterile adapter and sterile drape may be coupled together (e.g., as described above) during manufacturing, and packaged together as a sterile barrier for use during a robotic surgical procedure. In preparation for a surgical procedure, a user may couple the sterile adapter (e.g., frame) to an instrument driver such that each of one or more linearly displaceable drive members of the instrument driver may be received by an extensible cover and/or each of one or more rotary output drives may be coupled to a rotatable coupler (e.g., rotatable couplers 630a and 630b). The user may additionally arrange the sterile drape over the instrument driver and robotic arm, thereby forming a barrier between the instrument driver (and other non-sterile components) and the surgical instrument (and other sterile components or portion of a sterile environment).

The sterile drape may, in some variations, include a material that is flexible for blanketing or draping over desired components. The sterile drape may be substantially translucent or transparent (e.g., for enabling observation of components underneath the drape). For example, the sterile drape may include polypropylene and/or polyethylene. In some variations, the sterile drape may have a thickness of between about 0.05 mm and about 0.30 mm, between about 0.1 mm and about 0.2 mm, or any suitable thickness. The sterile drape may be attached to the sterile adapter (e.g., to the frame and/or flexible barrier) through thermal bonding, epoxy, etc. and/or any suitable manner.

Interlocked Arrangement

In some variations, the sterile barrier described herein may be used in combination with an interlocked arrangement configured to urge together a surgical instrument, the sterile adapter, and an instrument driver when the instrument driver actuates linearly displaceable drive members into or against the surgical instrument (e.g., during a robotic surgical procedure). Generally, as one or more actuated linear drive members of the instrument driver move linearly outward against drive inputs of a surgical instrument, a reaction force tends to undesirably separate the instrument driver and the surgical instrument (and/or tends to separate the instrument driver and the sterile adapter). The interlocked arrangement may be configured to advantageously leverage or transform such a reaction force into a compression force that urges together the instrument driver and the surgical instrument, thereby keeping the surgical instrument and the sterile adapter engaged with the instrument driver. Thus, generally, the greater the reaction force tending to separate the instrument driver and the surgical instrument, the greater the compression force counteracting the reaction force and urging the instrument driver and surgical instrument together (e.g., sandwiching the sterile adapter).

Figure 12:
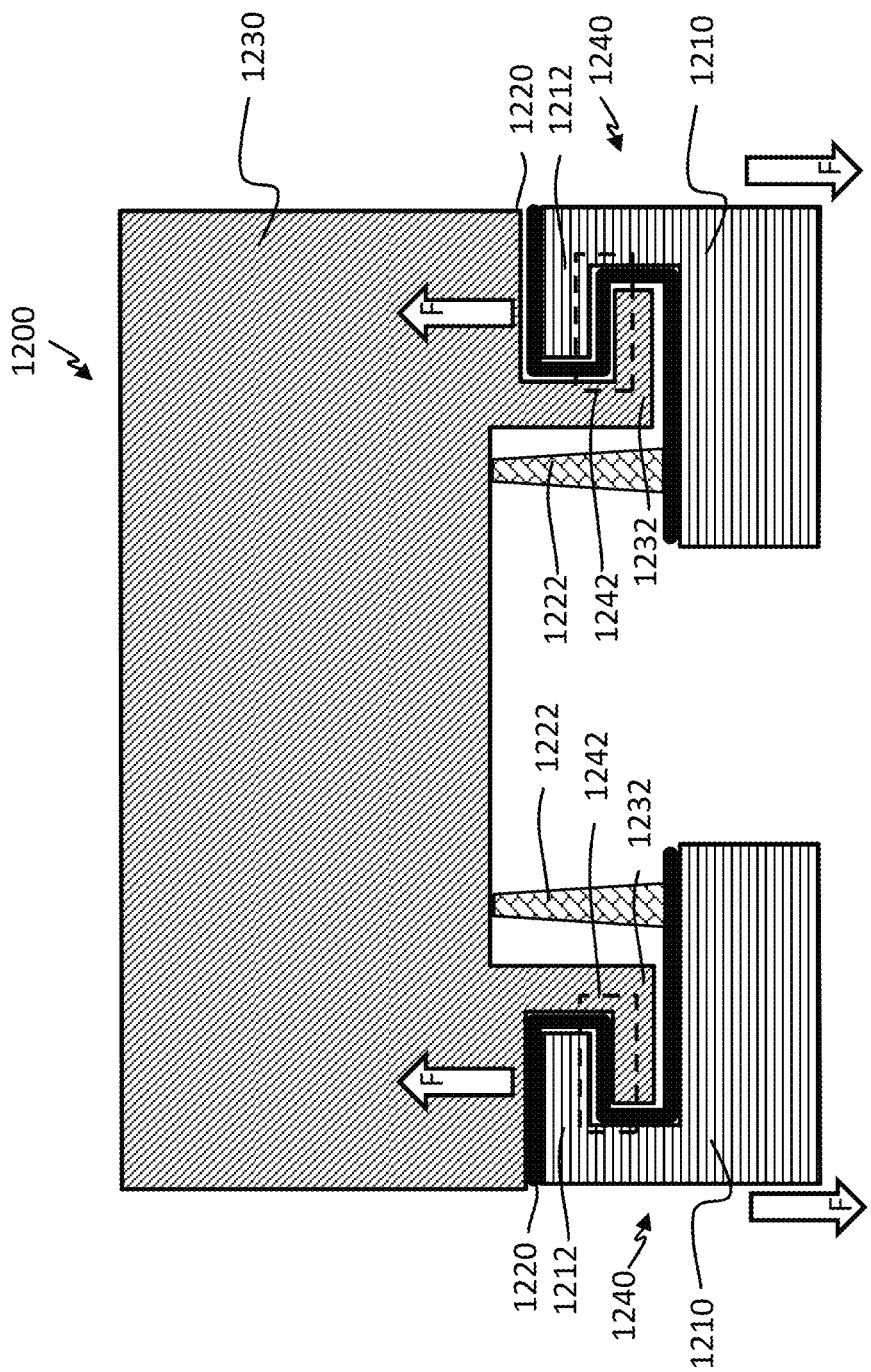
FIG. 12 is a schematic illustration of an exemplary variation of an interlocked arrangement.

Generally, in some variations, as shown in FIG. 12, a robotic surgical system 1200 may include an instrument driver 1210 (actuator) including at least one linearly displaceable drive member, a surgical instrument 1230 having at least one degree of freedom actuated by the at least one drive member, a sterile adapter 1220 interposed between the instrument driver 1210 and the surgical instrument 1230; and an interlocked arrangement 1240 coupling the instrument driver 1210 and the surgical instrument 1230 across the sterile adapter 1220, wherein the interlocked arrangement 1240 urges the instrument driver 1210 and the surgical instrument 1230 together when the instrument driver 1210 actuates the at least one degree of freedom of the surgical instrument 1230. For example, when the instrument driver 1210 actuates the at least one degree of freedom of the surgical instrument, a reaction force may tend to cause separation of the instrument driver 1210 and the surgical instrument 1230, as indicated by the arrows F. The interlocked arrangement 1240 may be configured to leverage or transform the reaction forces F into a compression force in the compression region 1242 that urges together the instrument driver 1210 and the surgical instrument 1230, thereby keeping the surgical instrument 1230 and the sterile adapter 1220 engaged with the instrument driver 1210.

In some variations, the instrument driver 1210 may be generally similar to the instrument drivers described above. For example, the instrument driver 1210 may include at least one (e.g., a plurality of) linearly displaceable drive member (not shown) similar to drive member 550b actuated by a linear actuator 524, as shown in FIG. 6D. Similarly, the surgical instrument 1230 may be generally similar to the instruments described above. For example, the surgical instrument 1230 may include one or more (e.g., a plurality of) drive inputs (not shown) such as flaps, levers, receptacles, or other mechanisms for receiving corresponding linearly displaceable drive members and actuating one or more degrees of freedom through a system of cables, belts, or other suitable driving elements. Furthermore, the sterile adapter 1220 may be generally similar to the sterile adapters described above. For example, the sterile adapter 1220 may include a frame, at least one (e.g., a plurality of) extensible covers 1222, and/or a flexible barrier, for being interposed between the instrument drive 1210 and the surgical instrument 1230.

However, in variations including an interlocked arrangement 1240, at least a portion of the instrument driver 1210 and/or at least a portion of the surgical instrument 1230 may comprise the interlocked arrangement. For example, the interlocked arrangement 1240 may include a first portion coupled to the instrument driver 1210 and a second portion coupled to the surgical instrument. In the exemplary schematic of FIG. 12, the interlocked arrangement 1240 may include a first interlocking member 1212 coupled to the instrument driver 1210 and a second interlocking member 1232 coupled to the surgical instrument 1230. Each of the first and second interlocking members may include one or more receiving surfaces (e.g., recess, hole, etc.) and/or one or more projecting surfaces that mutually engage so as to enable the first and second interlocking members to interlock or engage each other across the sterile adapter 1220. The sterile adapter 1220 may be shaped corresponding to the first and second interlocking members. For example, as shown in FIG. 12, each of the first and second interlocking members may be generally hook-shaped, and the hook shapes may engage each other across a sterile adapter 1220 that is generally "S" hook-shaped (or reverse "S" hook-shaped) to follow the contours of the interlocked, hook-shaped members. During operation of the robotic surgical system, linear actuation of the drive members may tend to separate the instrument driver 1210 and the surgical instrument 1230 apart, thereby loading the interlocked members 1212 and 1232 in tension. However, by virtue of the geometry of the interlocked arrangement 1240, the interlocked ends of the members 1212 and 1232 may be urged toward each other in the compression region 1242, thereby compressing the sterile adapter 1220 and increasing retention of the sterile adapter 1220 and the surgical instrument 1230.

Although FIG. 12 illustrates an interlocked arrangement 1240 including hook-shaped interlocking members, it should be understood that other kinds of interlocking or other coupling arrangements may leverage a reaction force (generated during actuation of a surgical instrument) into a force that urges together the instrument driver and the surgical instrument. For example, the first and/or second portions of the interlocked arrangement may include levers or pivoting members, pins insertable into receiving holes, or other suitable engaging elements.

Generally, the first and second portions of the interlocked arrangement may be engaged via snap fit or other suitable interference fit when the surgical instrument is coupled to the sterile adapter and instrument driver. In some variations, the first and second portions of the interlocked arrangement may be disengaged to permit decoupling of the instrument driver and the surgical instrument, when removal of the surgical instrument is desired. Furthermore, the first and second portions of the interlocked arrangement may be disengaged to permit removal of the sterile adapter which is otherwise interposed between the instrument driver and the surgical instrument. For example, after disengagement of the first and second portions of the interlocked arrangement and the subsequent removal of the surgical instrument from a central cavity of the instrument driver, the sterile adapter may be laterally squeezed toward the midline of the central cavity and removed, as described above with reference to FIG. 7B.

As shown in FIG. 13A, one example of an interlocked arrangement 1340 includes a first hook-shaped interlocking member 1312 coupled to an instrument driver 1310 and a second hook-shaped interlocking member 1332 coupled to a surgical instrument (not pictured). Similar to the interlocked arrangement described above with reference to FIG. 12, the first and second interlocking members 1312 and 1332 are configured to engage each other across a sterile adapter 1320, where sterile adapter 1320 may include a corresponding hook-shaped member 1324 interposed between the interlocking members 1312 and 1332. In some variations, members 1312 and 1324 (of the instrument driver and the sterile adapter, respectively) may be generally hooked laterally outwards while the member 1332 (of the surgical instrument) may be generally hooked laterally inwards. The interlocked arrangement (e.g., at formed at least in part by engagement between these hook-shaped members) may, for example, be created by pressing the sterile adapter onto the instrument driver, and pressing the surgical instrument onto the sterile adapter, thereby engaging and locking the interlocking members together via a snap fit or other suitable interference fit. During actuation of the surgical instrument, the region 1342 may be loaded in compression due to reaction forces as described above, thereby urging together the instrument driver, the sterile adapter, and the surgical instrument. Furthermore, disengagement of the interlocked arrangement may be performed, for example, by pivoting outward the surgical instrument member 1332 to separate it from the sterile adapter member 1324. After disengaging the interlocked arrangement, the surgical instrument may be separated and removed from the instrument driver. Thereafter, with the absence of the surgical instrument, as shown in FIG. 13B, a force indicated by arrow D (e.g., a laterally inward squeezing or pushing force) on the sterile adapter 1320 may cause lateral inward movement of the sterile adapter member 1324, thereby causing the sterile adapter member 1324 to disengage from the instrument driver member 1312 and permitting removal of the sterile adapter 1320 from the instrument driver 1310. Similar to that described above, the removal of the sterile adapter 1320 from the instrument driver 1310 may be substantially prevented when the surgical instrument is present and engaged with the instrument driver 1310. In some variations, the pushing force indicated by arrow D may be generated by a user directly pressing on the side of the sterile adapter, or operating latches, levers, or any suitable mechanism providing the force indicated by arrow D.

FIG. 14 illustrates another exemplary variation of an interlocked arrangement 1440. Similar to the interlocked arrangement 1340 described above with reference to FIGS. 13A and 13B, the interlocked arrangement 1440 includes a projection (e.g., a hook) coupled to the instrument driver 1410 and an interlocking member 1430 coupled to a surgical instrument 1430, where the interlocking member 1430 is configured to selectively engage or interlock with the projection on the instrument driver 1410. A sterile adapter 1420 may be interposed between the instrument driver 1410 and the surgical instrument 1430. The projection (of the instrument driver 1410) may be generally oriented laterally outwards, while the member 1430 (of the surgical instrument 1430) may be generally oriented laterally inwards. In this variation, the interlocking member 1430 may be actuatable up and down (e.g., by a user grasping the interlocking member 1430 on the sides of surgical instrument 1430 and sliding the member 1430) to disengage and engage the member 1430 with the instrument driver 1410. Furthermore, in some variations, the interlocking member 1430 may be operatively coupled to a switch, side grips, a handle, and/or other suitable grasping mechanism to facilitate moving the interlocking member 1430 in and out of the interlocked arrangement and thus, facilitate engagement and disengagement of the surgical instrument from the instrument driver.

Figure 15B:
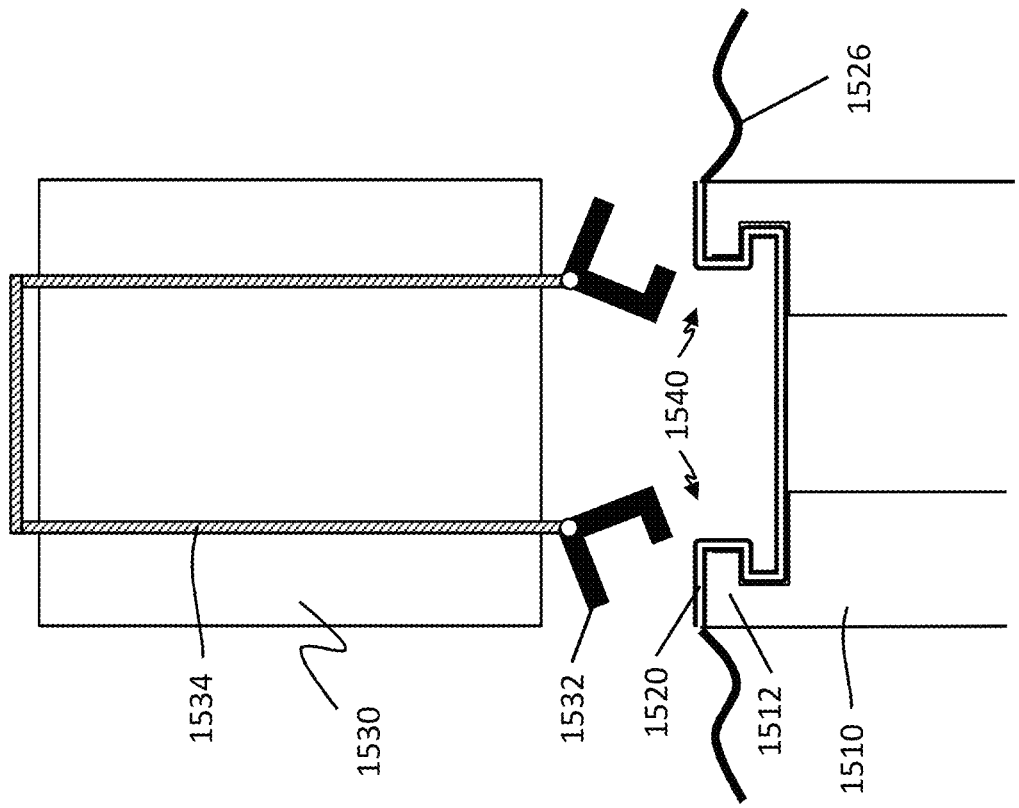
FIGS. 15A and 15B are schematic illustrations of another exemplary variation of an interlocked arrangement when engaged and disengaged, respectively.
Figure 15A:
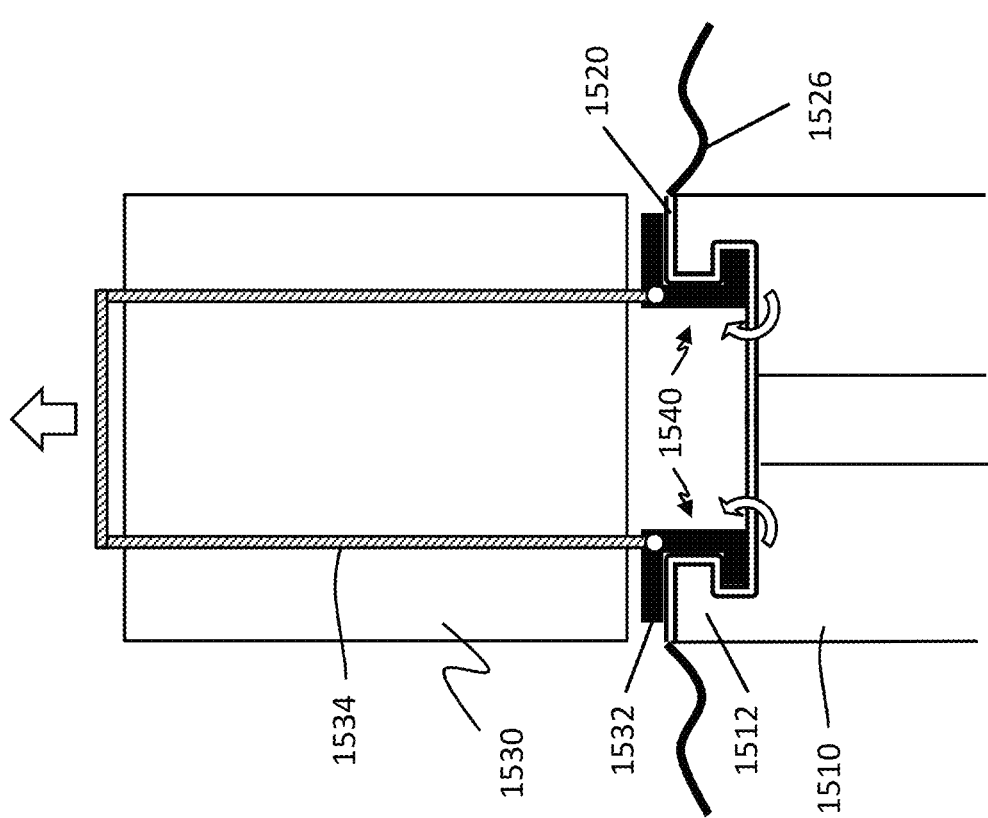

In some variations, at least a portion of the interlocked arrangement may be disengaged by a pivotable feature. For example, as shown in FIGS. 15A and 15B, an interlocked arrangement 1540 may include a first interlocking member 1512 coupled to an instrument driver 1510 and a second interlocking member 1532 coupled to a surgical instrument 1530. Generally, the first and second interlocking members 1512 and 1532 engage each other across a sterile adapter 1520, similar to the manner described above with reference to FIG. 12. Furthermore, a sterile drape 1526 may be coupled to the periphery of the sterile adapter 1532 and provide an additional barrier between the instrument driver 1510 and the surgical instrument 1530. However, in this variation, the second interlocking member 1532 is pivotable to facilitate engagement and disengagement from the first interlocking member 1512 similar to a latch. For example, the pivotable second interlocking member 1532 may be operatively coupled to a movable handle 1534. In FIG. 15A, the first and second interlocking members are engaged, such that the interlocked arrangement 1540 urges the instrument driver 1510 and the surgical instrument 1530 together when the instrument driver actuates the surgical instrument. A user may pull handle 1534 in a direction away from the instrument driver 1510 to cause the second interlocking member 1532 to pivot laterally inwards away from the first interlocking member 1512, thereby enabling disengagement of the interlocking arrangement 1540 and removal of the surgical instrument 1530 from the instrument driver 1510 as shown in FIG. 15B. It should be appreciated that such pivotable movement of the second interlocking member 1532 does not affect the positioning of the sterile adapter 1512, such that the sterile adapter 1512 may remain in place coupled to the surgical instrument (e.g., to facilitate instrument swapping without requiring replacement of the sterile adapter 1512). Furthermore, the direction of actuation of the handle required to facilitate removal of the surgical instrument may advantageously complementary (e.g., intuitive) to instrument removal, in that the user may move the handle in the direction intuitively required to separate the surgical instrument from the instrument driver. Although the handle 1534 is depicted in FIGS. 15A and 15B as a pull handle located on a "top" side of the instrument, it should be understood that other actuation mechanisms (e.g., side grips) may be used to actuate the pivotable second interlocking member 1532 similar to a latch.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:

1. A surgical robotic system, comprising:
   an actuator comprising at least one linearly displaceable drive member housed in an instrument mount interface;
   a surgical instrument having at least one degree of freedom actuated by the at least one linearly displaceable drive member, a portion of the surgical instrument being received in a cavity of the instrument mount interface;
   a sterile adapter interposed between the actuator and the surgical instrument, wherein the sterile adapter comprises a frame coupled to the instrument mount interface, a flexible barrier and an extensible cover integrally formed with the flexible barrier, wherein the extensible cover is arranged to receive the at least one linearly displaceable drive member, and the flexible barrier extends below the frame and below the extensible cover into the cavity of the instrument mount interface; and
   an interlocked arrangement coupling the actuator and the surgical instrument across the sterile adapter, wherein the interlocked arrangement urges the actuator and the surgical instrument together when the actuator actuates the at least one degree of freedom of the surgical instrument.

2. The system of claim 1, wherein the frame has a height measured as distance between the instrument mount interface and an instrument base of the surgical instrument that is at least as tall as the difference between a fully recessed position of the at least one linearly displaceable drive member and a fully extended position of the at least one linearly displaceable drive member.

3. The system of claim 2, wherein the flexible barrier conforms to the cavity; and the surgical instrument prevents decoupling of the actuator and the sterile adapter.

4. The system of claim 1, wherein the flexible barrier is co-injection molded with the frame.

5. The system of claim 1, wherein the extensible cover transitions between a rest state and a fully extended state in accordance with linear displacement of the at least one linearly displaceable drive member received in the extensible cover.

6. The system of claim 1, wherein the extensible cover comprises an elastomeric material.

7. The system of claim 1, wherein the extensible cover comprises an enclosed distal end; and wherein the enclosed distal end is reinforced.

8. The system of claim 7, wherein the enclosed distal end is thicker than a wall of the extensible cover.

9. The system of claim 7, wherein the enclosed distal end comprises a harder material than a wall of the extensible cover.

10. The system of claim 1, further comprising a sterile drape coupled to the sterile adapter.

11. The system of claim 1, wherein the interlocked arrangement comprises a first portion coupled to the actuator and a second portion coupled to the surgical instrument.

12. The system of claim 11, wherein the first portion comprises a first interlocking member and the second portion comprises a second interlocking member configured to engage with the first interlocking member.

13. The system of claim 11, wherein the second portion of the interlocked arrangement comprises a latch.

14. The system of claim 13, wherein the surgical instrument comprises a handle operatively coupled to the latch for releasably coupling the actuator and the surgical instrument.

15. The system of claim 14, wherein the latch is pivotable, and wherein the handle is operatively coupled to a fulcrum of the latch.

16. The system of claim 1, wherein the interlocked arrangement is configured such that when the actuator actuates the at least one degree of freedom of the surgical instrument and causes a reaction force, the interlocked arrangement leverages the reaction force into a compression force.

17. A sterile adapter for use in a surgical robotic system, the sterile adapter comprising:
    a frame configured to be coupled to an instrument mount interface in which an actuator that comprises a linearly displaceable drive member is housed, the linearly displaceable drive member being configured to actuate a degree of freedom of a surgical instrument when the surgical instrument is coupled to the instrument mount interface; and
    a flexible barrier, and an extensible cover integrally formed with the flexible barrier, wherein the extensible cover is arranged to receive the linearly displaceable drive member of the actuator, the flexible barrier being configured to extend below the frame and below the extensible cover into a cavity of the instrument mount interface in which a portion of the surgical instrument is received when the surgical instrument is coupled to the instrument mount interface.

18. The sterile adapter of claim 17 wherein the frame has a height measured as distance between the instrument mount interface and an instrument base of the surgical instrument that is at least as tall as the difference between a fully recessed position of the linearly displaceable drive member and a fully extended position of the linearly displaceable drive member.

19. The sterile adapter of claim 18 wherein flexible barrier conforms to the cavity.

* * * * *